United States Patent
Twilley et al.

(10) Patent No.: US 12,357,668 B2
(45) Date of Patent: Jul. 15, 2025

(54) **ANTICANCER ACTIVITY OF *BUDDLEJA SALIGNA* COMPOSITIONS**

(71) Applicant: University of Pretoria, Pretoria (ZA)

(72) Inventors: Danielle Twilley, Johannesburg (ZA); Namrita Lall, Pretoria (ZA)

(73) Assignee: University of Pretoria, Pretoria (ZA)

( * ) Notice: Subject to any disclaimer, the term of this patent is extended or adjusted under 35 U.S.C. 154(b) by 757 days.

(21) Appl. No.: 17/421,714

(22) PCT Filed: Jan. 21, 2020

(86) PCT No.: PCT/IB2020/050436
§ 371 (c)(1),
(2) Date: Jul. 8, 2021

(87) PCT Pub. No.: WO2020/152577
PCT Pub. Date: Jul. 30, 2020

(65) Prior Publication Data
US 2022/0088109 A1  Mar. 24, 2022

(30) Foreign Application Priority Data

Jan. 21, 2019 (ZA) .................................. 2019/00387

(51) Int. Cl.
| | | |
|---|---|---|
| *A61K 36/80* | (2006.01) | |
| *A61K 8/9789* | (2017.01) | |
| *A61K 31/19* | (2006.01) | |
| *A61P 35/00* | (2006.01) | |
| *A61Q 17/04* | (2006.01) | |

(52) U.S. Cl.
CPC ............ *A61K 36/80* (2013.01); *A61K 8/9789* (2017.08); *A61K 31/19* (2013.01); *A61P 35/00* (2018.01); *A61Q 17/04* (2013.01)

(58) Field of Classification Search
CPC ..................................................... A61P 35/00
See application file for complete search history.

(56) References Cited

FOREIGN PATENT DOCUMENTS

| CN | 104713829 A | 6/2015 |
|---|---|---|
| CN | 105497532 A | 4/2016 |
| CN | 108272690 A | 7/2018 |

OTHER PUBLICATIONS

Chukwujekwu et. al. (Antiplasmodial, acetylcholinesterase and alpha-glucosidase inhibitory and cytotoxicity properties of Buddleja saligna, South African Journal of Botany, 94 (2014) 6-8). (Year: 2014).*

Jadid et al., "Antioxidant Activities of Different Solvent Extracts of Piper Retrofractum Vahl. Using DPPH Assay", AIP Conference Proceedings, vol. 1854, Iss. 1, https://doi.org/10.1063/1.4985410, dated Jun. 26, 2017, 7 pages.

Alzeer et al., "The Influence of Extraction Solvents on the Anticancer Activities of Palestinian Medicinal Plants", Zurich Open Repository and Archive, DOI: https://doi.org/10.5897/JMPR2013.5044, dated 2014, 18 pages.

Reid, K. A., et al., "Evaluation of the mutagenic and antimutagenic effects of South African plants", Jour. Of Ethnopharmacology, Elsevier Ireland Ltd, vol. 106, No. 1, Jun. 15, 2006, pp. 44-50, 8pgs.

European Patent Office "Written Opinion", in application No. PCT/IB2020/050436, Mar. 13, 2020, 6pgs.

European Patent Office "Search Report", in application No. PCT/IB2020/050436, dated Mar. 13, 2020, 5 pages.

Dlova, N. C., et al., "Traditional and ethnobotanical dermatology practice in Africa", Clinics in Derm., Elsevier, vol. 36, No. 3, Mar. 10, 2018, pp. 353-362, 10pgs.

Alvarado, et al., "Nanoemulsion Strategy for Ursolic and Oleanic Acids Isolates from Plumeria ObtusaImproves Antioxidant and Cytotoxic Activity in Melanoma Cells", ACAMC Jan. 1, 2018, vol. 18, No. 6, 8pgs.

Afolayan, et al., "Ethnobotanical survey of medicinal plants used in the management of skin disorders among the Xhosa communities of the Amathole District, E. Cape—", Jour. Of Ethno. Feb. 28, 2014, 13pgs.

Adedapo, A., et al., "Assessment of the medicinal potentials of the methanol extracts of the leaves and stems of Buddleja saligna", BMC Complimentary and Alter. Med., vol. 9, No. 1, Jul. 6, 2009, 8pgs.

* cited by examiner

*Primary Examiner* — Terry A McKelvey
*Assistant Examiner* — Jacob A Boeckelman
(74) *Attorney, Agent, or Firm* — Patterson & Sheridan LLP.; Malgorzata A. Kulczycka

(57) ABSTRACT

The invention relates to an extract from *Buddleja saligna*, or a bioactive mixture consisting essentially of oleanolic acid and ursolic acid isolated from *Buddleja saligna*, for use in preventing and/or treating skin cancer, more specifically melanoma, and for reducing skin damage resulting from UV radiation. The invention also relates to uses and methods of treating skin cancer and reducing skin damage resulting from UV radiation using the extracts and/or bioactive mixture described. The invention further relates to an anticancer composition comprising the extracts and/or bioactive mixture, that inhibits angiogenesis and/or proliferation of cells associated with melanoma, as well as a sunscreen composition comprising the extracts and/or bioactive mixture.

7 Claims, 10 Drawing Sheets

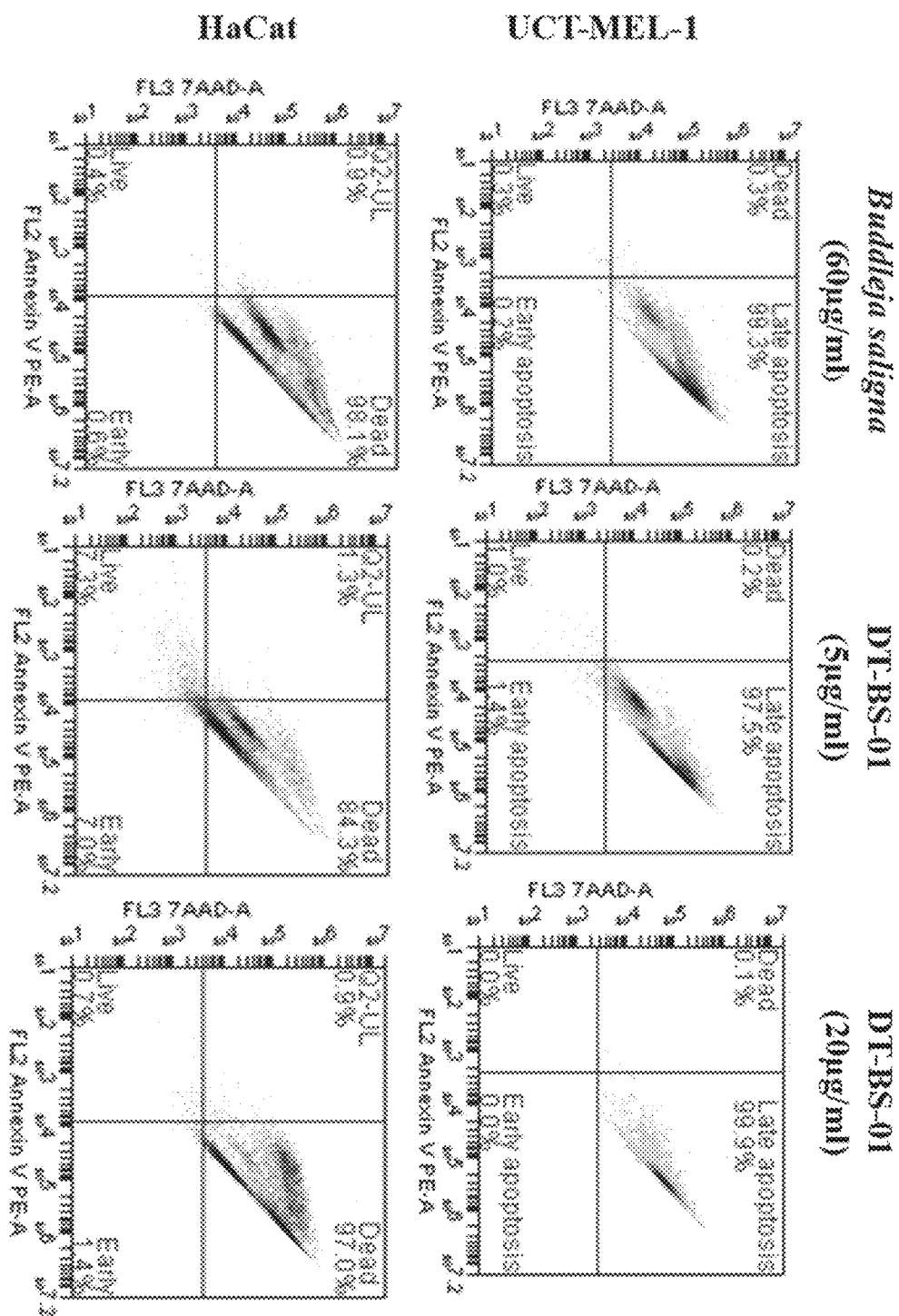
Figure 4 contd.

ANTICANCER ACTIVITY OF *BUDDLEJA SALIGNA* COMPOSITIONS

This application is a US National Stage Patent Application filed under 35 U.S.C. § 371 based upon International Patent Application No. PCT/162020/050436 filed Jan. 21, 2020, which claims the benefit of ZA Application 2019/00387 filed Jan. 21, 2019, the entire contents of all of which are hereby incorporated by reference as if fully set forth herein for all purposes.

BACKGROUND OF THE INVENTION

The present invention relates to extracts from *Buddleja saligna* and/or a bioactive mixture consisting essentially of oleanolic acid and ursolic acid isolated from *Buddleja saligna*, for use in methods of preventing and/or treating skin cancer, more specifically melanoma, and reducing skin damage resulting from ultraviolet (UV) radiation. The invention further relates to an anticancer composition comprising the extracts and/or bioactive mixture described, wherein the extract and/or bioactive mixture inhibits angiogenesis and/or proliferation of cells associated with melanoma, as well as a sunscreen composition having SPF activity which contains the extracts and/or bioactive mixture described. The invention also relates to uses and methods of preventing and/or treating skin cancer and reducing skin damage resulting from UV radiation using the extracts and/or bioactive mixture described.

Cancer accounts for one of the highest mortality rates worldwide. In 2012, the WHO estimated 8.2 million cancer deaths and 14 million cases. The death toll increased to 8.8 million in 2015 and is predicted to increase by 70% by 2035 to 24 million cases. Globally it is estimated that one in every six deaths is due to cancer. Over the past decades, the number of skin cancer cases has increased. An average 2-3 million new non-melanoma cases and 132,000 melanoma cases occur globally each year. A total of one in every three cancers diagnosed is a type of skin cancer.

In South Africa, more than 100,000 individuals are diagnosed with cancer each year and have an average survival rate of 6/10. It is predicted that cancer cases could increase by 78% by 2030. In South Africa, skin cancer is one of the most common types of cancer, annually about 20,000 individuals are diagnosed with non-melanoma skin cancer and 1,500 with melanoma, with an estimated 700 resulting in death due to melanoma.

One of the major hallmarks of melanoma is angiogenesis, the process of forming new blood vessels from existing ones, supplying the tumors with the oxygen and nutrients needed to grow, proliferate and metastasize. Melanoma develops in melanocytes, often in the form of a nevus or mole, which is a cluster of melanocytes. These nevi have the ability to transform into abnormal nevi, known as dysplastic nevi. Dysplastic nevi follow a radial growth phase pattern, in which the cells spread horizontally across the epidermis layer. Thereafter, cells are able to follow a vertical growth phase pattern in which cells enter into the dermis. During this transformation from radial to vertical growth phase, regulatory factors are secreted which induce angiogenesis, providing a route for the tumor cells to spread further into the body. In addition, another major route for metastasis (spread) to occur is through the lymphatic system. Once tumour cells have spread to the lymphatic vessels, they invade the lymph nodes giving access for the tumor cells to spread to the lungs, brain and liver.

The skin undergoes various immunological changes when exposed to ultraviolet (UV) radiation. UV radiation induces immunological responses, which increase rapid, uncontrollable growth of melanocytes, leading to a lack of oxygen and nutrients starving the cells (hypoxia). In response, regulatory factors are secreted which trigger angiogenesis.

There are a number of compounds currently undergoing clinical trials to inhibit angiogenesis, however there are currently no US Food and Drug Administration (FDA) approved anti-angiogenic drugs approved for the treatment of melanoma.

It has been reported that by inhibiting angiogenesis in tumor cells, this could enhance the effects of chemotherapy and radiation against the tumor, making the tumor more susceptible to treatment. In addition to this advantage, angiogenesis is often only required in the female reproductive cycle and for wound healing; therefore, the side effects are predicted to be limited to processes only involving angiogenesis.

There are many known regulatory factors which melanoma cells are able to secrete in order to trigger angiogenesis. Therefore, these regulatory factors provide promising targets to curb the spread of melanoma.

During the transformation of a dysplastic nevus from the radial growth phase to the vertical growth phase, the melanocytes secrete a high amount of vascular endothelial growth factor (VEGF) allowing for the growth of new blood vessels. This secretion of VEGF is continued throughout the growth of the new blood vessels.

In another study, it was found that interleukin-8 (IL-8) serum levels were higher in patients with melanoma as compared to healthy individual and the levels of IL-8 increased as the melanoma advanced. Both IL-8 secreted from the melanoma cells and from the endothelial cells are able to promote the growth and migration of melanoma. The over-expression of IL-8 has also been shown to increase angiogenesis, growth, metastasis and vascular permeability.

Melanoma cells generate larger amounts of reactive oxygen species (ROS) when compared to their surrounding tissue and are able to secrete the ROS into the surrounding environment. Nitric oxide (NO) is one example of such a free radical. Further, it is interesting to note that during normal circumstances the ROS produced during melanin synthesis are scavenged by the melanosomes, whereas in malignant melanoma the function of melanosomes seems to change and instead of scavenging ROS the melanosomes tend to produce ROS. It has further been reported that ROS contribute towards the metastatic potential of melanoma through increased synthesis of interleukin-8 (IL-8), increased levels of VEGF, activation of transcription factors such as nuclear-factor kappa Beta (NF-κB) and many other pathways.

Sphingosine kinase-1 (sphK1) is a lipid kinase, which phosphorylates sphingosine to produce sphingosine-1-phosphate. SphK1 is associated with the migration, differentiation, proliferation and cell survival. Sphk1 levels have been reported to be higher in melanoma cells, more specifically in vertical growth phase cell by 1.7-24 fold, when compared to melanocytes. An over-expression of sphK1 has been reported to increase the migration of melanoma cells.

Interleukin-6 (IL-6) is a cytokine, which plays a major role in the progression of cancer. It is able to inhibit apoptosis in tumor cells and increase angiogenesis. Metastatic melanoma cells have also been reported to have an increased expression of IL-6.

Cyclooxygenase-2 (COX-2) is an inducible enzyme, which is upregulated in various melanoma cell lines and has been shown to play a role in the metastasis of melanoma. One report speculates that VEGF expression is correlated to COX-2 expression and that the expression of these two factors is highly linked.

Accordingly, the inventors investigated whether a South African plant, *B. saligna*, and an isolated compound mixture from the plant (DT-BS-01) showed the potential to inhibit the abovementioned regulatory factors of angiogenesis, such as NO, COX-2, VEGF, IL-8, IL-6, and sphK1; and whether the extract and the DT-BS-01 mixture were able to induce apoptosis in melanoma cells.

SUMMARY OF THE INVENTION

The present invention relates to extracts from *Buddleja saligna* and/or a bioactive mixture consisting essentially of oleanolic acid and ursolic acid isolated from *Buddleja saligna*, for use in methods of preventing and/or treating skin cancer, more specifically melanoma, and reducing skin damage resulting from ultraviolet (UV) radiation.

According to a first aspect of the present invention there is provided for a crude or purified extract from *Buddleja saligna*, or a bioactive mixture consisting essentially of oleanolic acid and ursolic acid isolated or extracted from *Buddleja saligna*, for use in a method of preventing and/or treating skin cancer in a subject in need thereof. The crude or purified extract or bioactive mixture may also be used for reducing skin damage resulting from ultraviolet (UV) radiation in a subject. The skin cancer may be basal cell carcinoma, squamous cell carcinoma or melanoma, preferably malignant melanoma.

Specifically, when used in treating skin cancer, the extract or bioactive mixture inhibits angiogenesis and/or proliferation of cells associated with the skin cancer.

Preferably, the extract or bioactive mixture of the invention is an organic solvent-derived extract or a bioactive mixture obtained using an organic solvent. The organic solvent used to prepare or obtain the extract or bioactive mixture may be selected from the group consisting of ethanol, methanol, butanol, and mixtures thereof. Preferably, the organic solvent is ethanol.

Preferably, the subject is a mammal, in particular a human subject.

In one embodiment of the invention, the extract or bioactive mixture may further comprise a pharmaceutically acceptable carrier to obtain a pharmaceutical composition comprising the extract and/or bioactive mixture. The pharmaceutical composition may be formulated in a suitable form for administration to the subject by topical, parenteral, or oral administration. In particular, the pharmaceutically acceptable carrier may be a dermatologically acceptable carrier, the pharmaceutical composition may be a topical skin care composition and may be formulated for topical administration.

According to a second aspect of the present invention there is provided for a method of preventing and/or treating skin cancer in a subject in need thereof and/or a method of protecting skin of a subject against damage from ultraviolet (UV) radiation or reducing skin damage resulting from ultraviolet (UV) radiation, the method comprising administering to the subject a crude or purified extract from *Buddleja saligna* or a bioactive mixture consisting essentially of oleanolic acid and ursolic acid isolated from *Buddleja saligna*. The skin cancer may be basal cell carcinoma, squamous cell carcinoma or melanoma, preferably malignant melanoma.

Preferably, the method comprises administering the extract or bioactive mixture together with a pharmaceutically acceptable carrier as a pharmaceutical composition, in a suitable form for administration to the subject by topical, parenteral, or oral administration. In particular, the pharmaceutical composition for protecting skin of a subject against damage from ultraviolet (UV) radiation or reducing skin damage resulting from ultraviolet (UV) radiation may be a topical skin care composition and may be formulated for topical administration.

According to a third aspect of the present invention there is provided for the use of a crude or purified extract from *Buddleja saligna* or a bioactive mixture consisting essentially of oleanolic acid and ursolic acid isolated from *Buddleja saligna*, in the manufacture of a medicament for use in a method of treating skin cancer in a subject in need thereof and/or a method of protecting skin of a subject against damage from ultraviolet (UV) radiation.

In a fourth aspect of the present invention there is provided for an anticancer composition comprising a crude or purified extract from *Buddleja saligna* or a bioactive mixture consisting essentially of oleanolic acid and ursolic acid isolated from *Buddleja saligna*, wherein the extract or bioactive mixture inhibits angiogenesis and/or proliferation of cells associated with melanoma, preferably malignant melanoma.

According to yet a further aspect of the present invention there is provided for a sunscreen composition comprising a crude or purified extract from *Buddleja saligna* or a bioactive mixture consisting essentially of oleanolic acid and ursolic acid isolated from *Buddleja saligna*, wherein the extract or bioactive mixture has sun protection factor activity. Preferably, the sunscreen composition is formulated for topical administration to a subject.

In another aspect of the invention, there is provided for a cosmetic method of protecting the skin of a subject from skin damage from ultraviolet (UV) radiation, the method comprising administering to the subject a crude or purified extract from *Buddleja saligna* or a bioactive mixture consisting essentially of oleanolic acid and ursolic acid isolated from *Buddleja saligna*.

Preferably, the cosmetic method comprises administering the extract or bioactive mixture together with a dermatologically acceptable carrier as a composition in a suitable form for topical administration to the subject.

BRIEF DESCRIPTION OF THE FIGURES

Non-limiting embodiments of the invention will now be described by way of example only and with reference to the following figures.

DETAILED DESCRIPTION OF THE INVENTION

Figure 1:
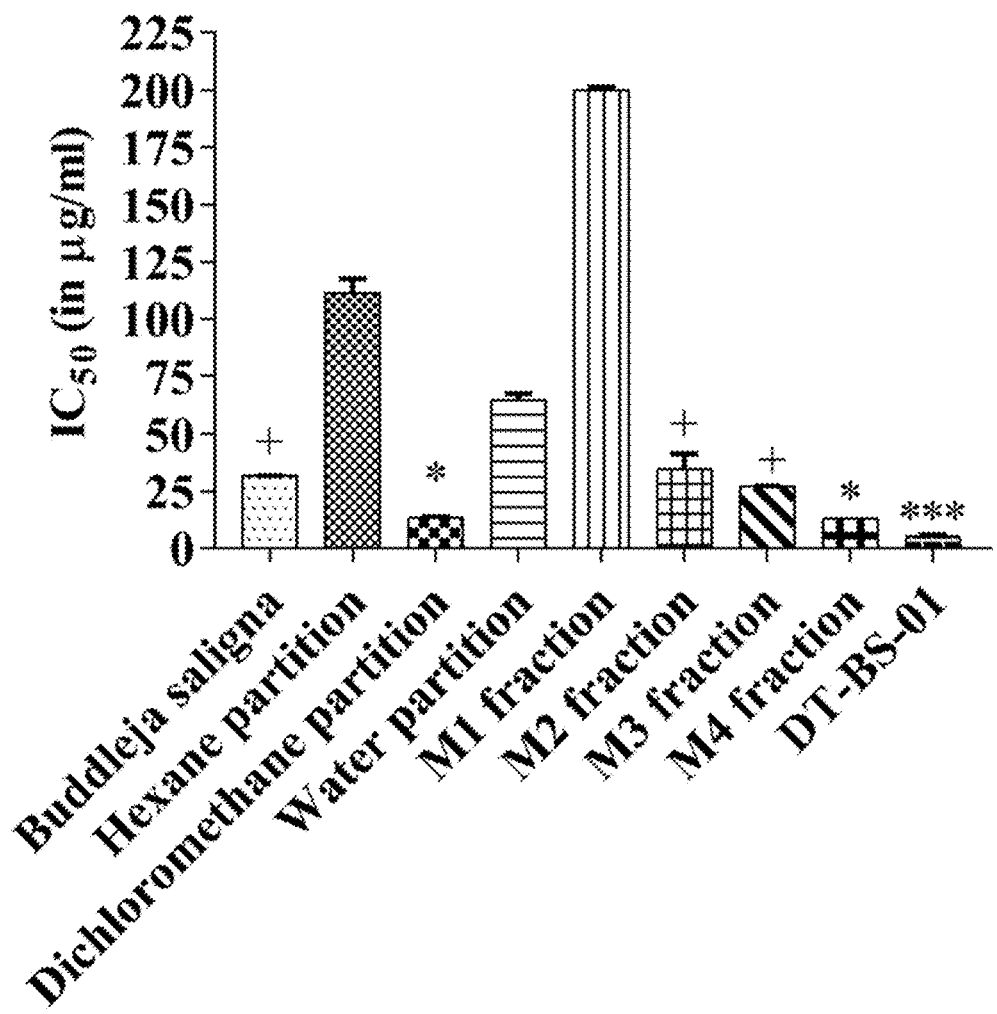
FIG. 1: Fifty percent inhibitory concentrations ($IC_{50}$) against human melanoma (UCT-MEL-1) cells. Data shown are mean±SD (n=3). *B. saligna* was used for comparison as it showed statistically similar (P>0.05) activity to the guidelines set by the American Cancer Institute, which sets the limit of activity for an extract at an $IC_{50}$<30 µg/ml after 72 h exposure. Samples statistically similar to *B. saligna* were identified with (+) and therefore had good activity. *P<0.05 and ***P<0.001 compared with *B. saligna* (+) showed statistically significant activity. Statistical analysis was done using one-way analysis of variance (ANOVA) followed by Tukey's multiple comparison test using the GraphPad Prism statistical software.

The present invention will now be described more fully hereinafter with reference to the accompanying drawings, in which some, but not all embodiments of the invention are shown.

The invention as described should not be limited to the specific embodiments disclosed and modifications and other embodiments are intended to be included within the scope of the invention. Although specific terms are employed herein, they are used in a generic and descriptive sense only and not for purposes of limitation.

As used throughout this specification and in the claims which follow, the singular forms "a", "an" and "the" include the plural form, unless the context clearly indicates otherwise.

The terminology and phraseology used herein is for the purpose of description and should not be regarded as limiting. The use of the terms "comprising", "containing", "having" and "including" and variations thereof used herein, are meant to encompass the items listed thereafter and equivalents thereof as well as additional items.

The present invention relates to the use of crude or purified extracts from *Buddleja saligna* and/or a bioactive mixture comprising oleanolic acid and ursolic acid isolated from *Buddleja saligna* in treating skin cancer and reducing skin damage resulting from UV radiation. The invention further relates to anticancer compositions comprising the extracts and/or bioactive mixture, wherein the extract and/or bioactive mixture inhibits angiogenesis and/or proliferation of cells associated with melanoma, as well as a sunscreen composition having SPF activity containing the extracts and/or bioactive mixture.

Angiogenesis is one of the major hallmarks of cancer, including melanoma. Melanoma cells, as well as many other types of cancers, have the ability to upregulate and secrete various regulatory factors which induce angiogenesis thereby allowing an increase in growth, proliferation and metastasis. Factors that induce angiogenesis provide a key target for the treatment of melanoma. The inventors of the present invention evaluated an ethanolic extract of the leaves and stems of *B. saligna* for its antiproliferative activity against human melanoma cells. A bioactive compound mixture (DT-BS-01) was isolated from the extract, which was identified as a mixture of oleanolic acid and ursolic acid. Both the extract and the compound mixture showed significant antiproliferative activity against melanoma cells.

The extract and the bioactive compound mixture were also tested for their apoptotic effect on melanoma and their effect on various regulatory factors associated with angiogenesis. Both the extract and the bioactive compound mixture were able to induce apoptosis. Moreover, the extract moderately inhibited cyclooxygenase-2 (COX-2) and nitric oxide (NO). Similar results were obtained for the bioactive compound mixture. *B. saligna* ethanolic extract and the bioactive mixture were both further able to moderately inhibit sphingosine kinase-1 (sphK1). Significant inhibition of interleukin-8 and -6 (IL-8, IL-6) and the vascular endothelial growth factor (VEGF) was noted for both *B. saligna* and the bioactive compound mixture. Furthermore, a sunscreen formulation containing 10% (v/v) of *B. saligna* extract (6.0 mg/ml) showed an SPF of 16 in an in vivo clinical trial and showed protection against UVA.

Taken together, the results of this study show that the extract of *B. saligna* is able to effectively inhibit the proliferation of melanoma cells, as well as factors related to an increase in angiogenesis. Furthermore, the use of ursolic acid and oleanolic acid in combination reveals the potential of a synergistic or addictive effect against melanoma and angiogenesis. This is the first report known to the inventors on the antiproliferative activity of *B. saligna* against melanoma cells as well as against a human cancer cell line, the combined antiproliferative activity of ursolic acid and oleanolic acid against UCT-MEL-1 cells and the activity of *B. saligna* and the triterpenoid mixture against these angiogenic factors and on the specific cell lines. During qualitative measurements, morphological changes in the cells were observed which are characteristic of apoptosis, such as membrane blebbing, apoptotic body formation, nuclear fragmentation and condensed chromatin.

It will be understood that the extract of the invention may be in the form of a crude extract, a purified extract or a pharmaceutical composition.

As used herein the term "crude extract" refers to a concentrated preparation of a plant extract obtained by removing secondary metabolites from the crude plant material with the aid of a suitable solvent. This may be done, for example, by submerging the crude plant material in a suitable solvent, removing the solvent and consequently evaporating all or nearly all of the solvent. As used herein the term "purified extract" refers to an extract obtained by separating the constituent parts of the crude extract from each other. By way of a non-limiting example, the constituent parts of the crude extract may be separated from one another by separating the polar constituents from the non-polar constituents. In so doing the active polar and/or non-polar constituents may thus be concentrated.

Those skilled in the art will appreciate that there are a number of methods for synthesizing extracts from crude plant material. These methods include, among others, cutting, chopping, macerating and/or grinding raw plant material to at least one solvent in order to obtain a plant extract. It will also be appreciated that the crude plant material may be fresh material or dry plant material.

The solvent may be an organic solvent. Organic solvents typically used in the preparation of plant extracts include but are not limited to ethanol, methanol, butanol dichloromethane, chloroform, acetone and/or mixtures thereof.

Any appropriate route of administration may be employed, such as, parenteral, intravenous, subcutaneous, intramuscular, intracranial, intraorbital, ophthalmic, intraventricular, intracapsular, intraspinal, intrathecal, intracisternal, intraperitoneal, intranasal, aerosol, topical, or oral administration.

As used herein the term "subject" includes a mammal, preferably a human or animal subject, but most preferably the subject is a human subject.

"Suitable forms" of the pharmaceutical composition for topical use may include, for example, sprays, lotions, creams, essences, toners, emulsions, soaps, shampoos, rinses, cleansers, solutions, ointments, balm, oil, jellies, suspensions, or solid, such as a roll-on, for personal use, or a solid strip. For instance, sprays can be prepared using conventional propellants, such as propane, butane, isobutane, either alone or in various mixtures known to those skilled in the art. The suitable forms of the pharmaceutical composition for topical use may be combined with pharmaceutically acceptable carriers and other elements known in the art to produce creams and lotions for use for general skin care. The pharmaceutical composition may further be combined with other ingredients, which promote absorption by the skin. Suitable forms of the pharmaceutical composition for oral use may include, for example, tablets, capsules, tinctures, powers, inhalants and/or liquids.

Other pharmaceutically acceptable ingredients may be used with the extracts or pharmaceutical compositions of the invention. The term "pharmaceutically acceptable" refers to properties and/or substances which are acceptable for administration, such as topical, parenteral, or oral administration, to a subject from a pharmacological or toxicological point of view. Further, "pharmaceutically acceptable" refers to factors such as formulation, stability, patient acceptance and bioavailability which will be known to a manufacturing pharmaceutical chemist from a physical/chemical point of view.

By "pharmaceutically acceptable carrier" is meant a solid or liquid filler, diluent or encapsulating substance which may be safely used for the administration of the extract, mixture, pharmaceutical composition and/or medicament to a subject.

It will be appreciated that the crude or purified extract, bioactive mixture and/or pharmaceutical composition comprising the crude or purified extract may also be used in applications for animal and veterinary products.

The pharmaceutical compositions, extracts, mixtures and compounds of the invention can be provided either alone or in combination with other active compounds (for example, small molecules, nucleic acid molecules, peptides, or peptide analogues).

The use of the extracts, bioactive mixtures or pharmaceutical compositions or methods of treatment and/or prevention using the extracts, mixtures or pharmaceutical compositions entails administration of an effective amount of the extract or a pharmaceutical composition or extract to a subject in order to prevent or treat a condition or to reduce skin damage resulting from ultraviolet radiation. The term "effective amount" in the context of preventing or treating a condition or reducing skin damage resulting from ultraviolet radiation refers to the administration of an amount of the active plant extract or the pharmaceutical composition containing the bioactive mixture or compounds to an individual, either a single dose or several doses of the extract, mixture or pharmaceutical composition containing the extract or the bioactive compound mixture, to achieve the desired therapeutic result.

Any of the compositions of the invention may be administered in a single dose or in multiple doses. Although some indications have been given as to suitable dosages of the extract, mixture and/or pharmaceutical composition containing the extract or mixture, the exact dosage and frequency of administration of the effective amount will be dependent on several factors. These factors include the individual components used, the formulation of the extract or pharmaceutical composition containing the extract, the nature and severity of the condition, the age, weight, health and general physical condition of the subject being treated, and other medication that the subject may be taking, and other factors as are known to those skilled in the art. It is expected that the effective amount will fall within a relatively broad range that can be determined through routine trials.

Dosage values may vary and be adjusted over time according to the individual need and the judgment of the person administering or supervising the administration of the extracts or pharmaceutical compositions of the invention.

The term "cancer" refers to the physiological condition in an individual that is typically characterized by unregulated cell growth. Preferably, the cancer is skin cancer, more preferably basal cell carcinoma, squamous cell carcinoma or malignant melanoma.

The following chemicals and reagents were obtained and used in the examples provided below and the following statistical analyses were performed:

Reagents

The UCT-MEL-1 (human pigmented melanoma) and HaCat (human keratinocytes) cell lines were donated by Dr Lester Davids from the Department of Human Biology, University of Cape Town. The VEGF ELISA kit, cell culture medium, trypsin-EDTA, phosphate buffer saline (PBS), fetal bovine serum and antibiotics were purchased from ThermoFisher Scientific® (Johannesburg, South Africa). Sterile cell culture plates and flasks were obtained from Lasec SA (Pty) Ltd (Midrand, South Africa). The Annexin-V FITC apoptosis detection kit, BD™ Cytometric Bead Array (CBA) Human Inflammatory Cytokine kit, BD Cytofix™ fixation buffer and the BD Phosflow™ permeation buffer were purchased from BD Biosciences®, San Jose, CA, USA. The $PGE_2$ ELISA kit and the FITC-labelled sphK1 antibody were purchased from Biocom Biotech (Pty) Ltd (Pretoria, South Africa). The Cell Proliferation Kit II (XTT) as well as all other chemicals and reagents, including: Actinomycin D (purity≤95%), ascorbic acid (purity≤99%), oleanolic acid (purity≤97%), ursolic acid (purity≤90%) and human cyclooxygenase-2 enzyme, were purchased from Sigma® Chemicals Co. (St. Louis, MO, USA).

Statistical Analyses

All results are reported as mean±SD (n=3). Statistical analysis was done using one-way analysis of variance (ANOVA) followed by Tukey's Multiple Comparison Test or Dunnett's Multiple Comparison Test to determine statistical significance using the GraphPad Prism statistical software. *P<0.05; P<0.01 and *P<0.001 indicated statistical significance compared to the control (+). Samples which were statistically similar in activity to the controls were identified (+). For cancer cell antiproliferative activity, $IC_{50}$ values were compared to that of B. saligna (31.80±0.35 µg/ml). B. saligna was used for comparison as it showed statistically similar (P>0.05) activity to the guidelines set by the American Cancer Institute, which sets the limit of activity for an extract at an $IC_{50}$<30.00 µg/ml after 72 h exposure (Steenkamp & Gouws, 2006). Samples statistically similar to B. saligna were identified with (+) and therefore had good activity. For the SPF test the data was expressed as mean SPF±SD (n=10). The data was analyzed by using the t test to determine whether the mean of the sunscreen formulation containing B. saligna was statistically similar to that of the standard.

The following examples are offered by way of illustration and not by way of limitation.

Example 1

Extract Preparation and Bioactive Isolation

Plant Collection

Leaves and stems of B. saligna (Willd.) were collected in February 2015 from the Manie van der Schijff Botanical Gardens, University of Pretoria, South Africa. The plant material was identified by the curator, Mr Jason Sampson, and a voucher specimen (122167) was deposited in the HGWJ Schweickerdt Herbarium, Pretoria, South Africa. The plant material was shade dried at room temperature and powdered using an IKA MF 10 universal grinder. Upon shade drying there was a 56.5% loss of moisture.

Preparation of Plant Extract

The powdered plant material (1.66 kg) was extracted using absolute ethanol (9 L) and left on a shaker for 72 h. The extract was filtered through a Büchner funnel using Whatman® no. 1 filter paper. The extraction and filtration procedure was repeated another two times with 5 L and 4 L of absolute ethanol respectively. The solvent from the three extractions were combined and evaporated under reduced pressure at 45° C. using a Büchi Rotavapor R-200 to obtain 200 mL of solvent. The remaining 200 mL of solvent was freeze dried for 2 weeks to obtain 240.68 g of dry extract (14.5% yield). The extract was kept at 4° C. until further use.

Liquid-Liquid Partitioning of Extract

Figure 4:
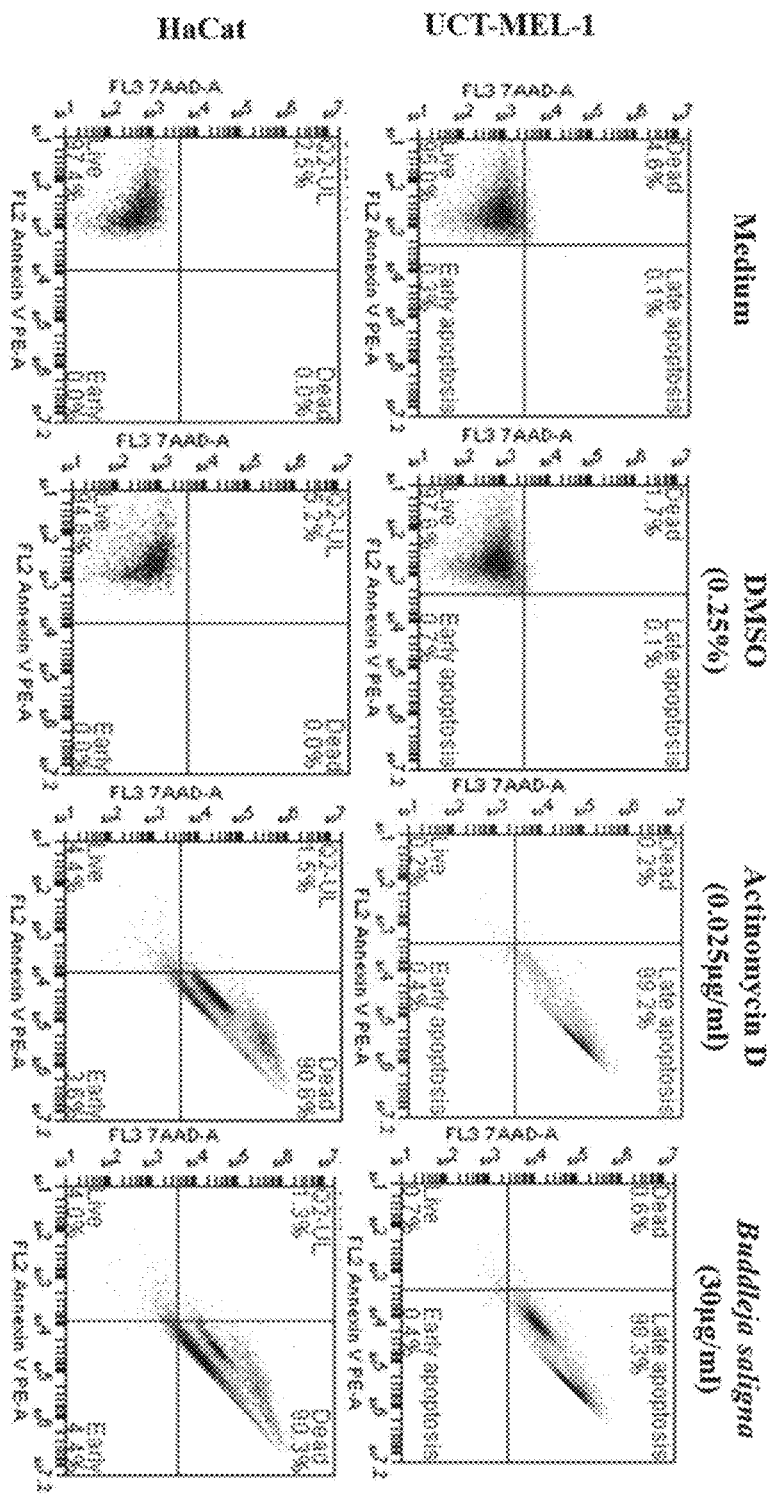
FIG. 4: Apoptosis of human melanoma (UCT-MEL-1) and human keratinocyte (HaCat) cells was measured by Annexin V and 7-AAD staining after 48 h following various treatments with *B. saligna* and DT-BS-01.

Partitioning of the crude extract was done according to a method described by Chukwujekwu et al (2013). Partitioning was done by dissolving the crude ethanol extract (160 g) in 100% methanol (500 mL) followed by extraction with hexane (8×500 mL) in a separating funnel. The hexane layers were combined and evaporated under reduced pressure at 40° C. using a Büchi Rotavapor R-200 to obtain 11.45 g of the hexane partition. The remaining methanol layer was concentrated in the same manner and the dried extract (145 g) was re-dissolved in distilled water (250 mL) by sonication for 30 min. The re-dissolved water partition was extracted with dichloromethane (DCM) (4×400 mL) in a separating funnel. The DCM layers were combined and dried under reduced pressure to obtain 22.12 g of the DCM partition. The water partition was freeze dried for 1 week to obtain 40.29 g. The three partitions (hexane, DCM and water) were tested for antiproliferative activity against malignant melanoma (UCT-MEL-1) cells to determine which partition to use for bio-assay guided fractionation. The partitions were tested for antiproliferative activity against UCT-MEL-1 cells with $IC_{50}$ values of 111.65±10.3, 13.68±0.16 and 64.87±4.78 for the hexane, DCM and water partition respectively (FIG. 4.2). The DCM partition showed significant (P<0.05) antiproliferative activity against UCT-MEL-1 cells and therefore, was selected for further isolation.

Bioassay-Guided Fractionation

Due to the bioactivity of B. saligna against human melanoma cells (UCT-MEL-1), chromatographic separation was performed using silica and sephadex LH 20, to yield a bioactive compound (DT-BS-01). The dried DCM partition (12 g) was re-dissolved in 50 mL of DCM and mixed with silica gel as the stationary phase to form a slurry. The dried slurry was placed on a column packed with silica gel. The column was eluted with a mixture of hexane:DCM of increasing polarity (100:0 to 0:100) followed by hexane: ethyl acetate of increasing polarity (100:0 to 0:100) and ethyl acetate:methanol of increasing polarity (100:0 to 0:100). A total of 66 major fractions were collected and pooled together according to similarity in thin-layer chromatographic (TLC) profiles. The major fractions were combined into 4 sub-fractions (M1, M2, M3 and M4). M4 showed the highest antiproliferative activity towards UCT-MEL-1 cells ($IC_{50}$: 13.08±0.02 µg/ml) and therefore, was subjected to further isolation. M4 (907 mg) was chromatographed on sephadex LH-20 column using DCM:methanol as the eluent from which 14 sub-fractions were collected and pooled together based on TLC profile. Sub-fraction 1-9 (410 mg) were combined and subject to silica gel chromatography with DCM:methanol at a 98:2 ratio as an eluent, which yielded an amorphous white powder, compound 1; DT-BS-01 (C1; 38 mg), which migrated as a single spot on the TLC plate. Upon identification of DT-BS-01 by $^1$H and $^{13}$C NMR (400 MHz Bruker Avance II; 5 mm BBO probe) spectroscopic data as well as COSY, HSQC, HMBC and LC-MS it was found to be a mixture of two pentacyclic triterpenoids; oleanolic acid (OA) and ursolic acid (UA) which was obtained as a white powder. As these structures are structurally similar, it was observed as one spot on the TLC plate.

Liquid Chromatography—Mass Spectrometry (LC-MS) Analysis

To confirm the identified structures, standards were purchased (ursolic acid, purity>90% and oleanolic acid, purity>97%; Sigma Aldrich, St. Louis, Mo., USA) and NMR ($^1$H and $^{13}$C) and LC-MS spectra obtained and compared to that of the isolated mixture. The spectra of the isolated mixture were in agreement with the standards.

LC-MS analysis of DT-BS-01, and the reference standards oleanolic acid and ursolic acid was performed using a Waters® Acquity UPLC system with a binary solvent system (Waters Corp., MA, USA) coupled to a Waters Synapt G2 mass spectrometry. Separation was performed on a Kinetex® 1.7 μm EVO C18, 2.1 mm×100 mm column was set at 40° C. and the flow rate was kept constant at 0.35 mL/min, with an injection volume of 7 μl. The mobile phase consisted of A: 0.1% formic acid in purified water and B: methanol with 0.1% formic acid. A total run time of 25 min was used following a gradient elution method as follows: 20% B (0.0 min); 100% B (15-22 min); 20% B (23-25 min). The mass spectrometry (MS) was operated in positive and negative ESI resolution mode. Nitrogen gas was used as desolvation gas. MS data was acquired between 50 and 1200 m/z. The following parameters were set: Capillary voltages of 2600 V; sampling cone voltages of 30 V; extraction cone was 4 V; source temperature was 120° C.; desolvation temperature was 300° C.; desolvation gas 600 L/hr; Cone Gas flow 10.0 L/hr. Throughout all acquisitions, a 2 ng/μl solution of leucine enkephalin was used as the lockspray solution that was constantly infused at a rate of 5 μl/min through a separate orthogonal ESI probe so as to compensate for experimental drift in mass accuracy. The complete system was driven by Masslynx software.

Gas Chromatography—Mass Spectrometry (GC-MS) Analysis

Sub-fractions M1, M2 and M3 as well as the ethanol extract of *B. saligna* were further submitted for GC-MS analysis. GC-MS analysis of the ethanol extract of *B. saligna*, as well as the sub-fractions (M1, M2 and M3) obtained from bio-assay guided fractionation, was performed using a LECO Pegasus 4D GC-TOFMS (LECO Africa (Pty) Ltd., Kempton Park, South Africa) including an apolar Rxi-5SiMS (30 m×0.25 mm ID×0.2 μm film thickness) (Restek, Bellefonte, Pa., USA) capillary column. Ultra-high purity grade helium (99.999%) (Afrox, Gauteng, South Africa) was used as a carrier gas at a constant flow rate of 1 ml/min. The injector temperature was maintained at 250° C. and the inlet was operated in a splitless mode (splitless time 30 s). The GC oven temperature programme was 40° C. (3 min) at 10° C./min to 300° C. (5 min). The MS solvent delay was 5 min, and the total GC-MS running time was 36 min. The MS transfer line temperature was set at 280° C. and the ion source temperature was set at 230° C. The electron energy was 70 eV in the electron impact ionization mode (EI+), the data acquisition rate was 10 spectra/s, the mass acquisition was 40-550 Daltons, and the detector voltage was set at 1750 V.

GC-MS analysis is used to separate volatile compounds within a complex sample and provides a tentative identification of compounds present in a sample. GC-MS chromatogram analysis of the ethanol extract of *B. saligna* and its isolated major fractions (M1, M2 and M3) showed multiple peaks indicating the presence of numerous phytochemical compounds. The mass spectra of the constituents where compared to the NIST08 Mass Spectral Library to characterize and identify the compounds present within the different samples depending on their similarity to the library database. The retention time (RT), molecular formula, molecular weights, concentration (peak area %) and similarity to the NIST08 library was determined for the identified compounds (data not shown).

In the ethanol extract of *B. saligna*, four different chemical compounds were identified, of which oleanolic acid was the most prevailing compound (55.05%), which was also isolated as a mixture from major fraction M4 and found to be present in M3. In major fraction M1, 79 compounds were identified; however, some compounds were the same such as; heptacosan, dotriacontane, and hexatricontane appearing at different retention times. The major compounds within M1, were dotriacontane (16.56%), hexatricontane (14.89%), decanoicacid, ethyl ester (8.41%), heptacosane (7.48%), 6,10-dimethyl-2-undecanone (5.63%) and 1 unknown compound with the molecular formula $C_{19}H_{34}O_5Si_3$ (11.58%). M2, consisted of 76 various compounds, of which 6,10-dimethyl, 2-undecanone (8.21%), 3-octadecyne (6.16%), phytol (6.16%) and aromadendrene oxide-(2) (4.27%) were the main constituents. In M3, only 34 compounds were identified of which heptacosane, 3,6-dimethyl, 1-octen-2-one, and 1,2,4,5-tetramethyl benzene each appeared twice at different retention times. The main constituents found were oleanolic acid (32.03%), hexadecanoic acid, butyl ester (5.76%), 4-hydroxy-3-methyl-2-butenyl acetate (8.0%) and 2,7,7-trimethyl-3-oxatricyclo [4.1.1.0 (2,4)] octane (5.36%).

Example 2

Antiproliferative Activity

Cell Viability

The cell lines were maintained in culture flasks containing Dulbecco's modified Eagle's medium (DMEM) supplemented with 10%, heat-inactivated fetal bovine serum (FBS) and 100 U/ml penicillin, 100 μg/ml streptomycin and 250 μg/ml fungizone at 37° C. and 5%, $CO_2$. Cells were sub-cultured once an 80%, confluent monolayer had formed using trypsin-EDTA (0.25%, trypsin containing 0.01%, EDTA).

To investigate the antiproliferative potential of *B. saligna* and DT-BS-01, the XTT assay was performed. Antiproliferative activity was measured using the method as described by Berrington and Lall (2012) using the XTT Cell Proliferation Kit II. Cells were seeded at a concentration of $1.0×10^6$ cells/ml in 96-well plates (100 μl) and allowed to adhere for 24 h. The *B. saligna* extract and DT-BS-01 were prepared at stock concentrations of 20 mg/ml, serially diluted and added to the 96-well plates at final concentrations ranging from 1.56-200 μg/ml. Controls included a 2% DMSO vehicle control, cells grown in medium only and Actinomycin D at final concentration ranging from $3.9×10^{-4}$-0.05 μg/ml. Cells were incubated for a further 72 h with the respective samples and controls. Thereafter, 50 μl XTT (0.3 mg/ml) was added to the cells and incubated for 2 h where after the absorbance was measured at 490 nm (reference wavelength of 690 nm) using a BIO-TEK powerwave XS plate reader (A.D.P, Weltevreden Park, South Africa). Blank plates were included which were prepared in the same manner as mentioned above, without the additional of cell, to allow for colour compensation of the samples. The samples were tested in triplicate and the percentage cell viability was calculated using the following equation.

$$\% \text{ Viability} = \frac{\text{Abs sample}}{\text{Abs control}} \times 100$$

Where $\text{Abs}_{control}$ is the absorbance of XTT+vehicle control and $\text{Ab}_{sample}$ is the absorbance of (XTT+sample OR positive control)–(blank values of corresponding sample). The fifty percent inhibitory concentrations ($IC_{50}$) were calculated from the % cell viability using the GraphPad Prism 4 software.

The XTT colorimetric assay is based on the ability of viable metabolically active cells to convert a yellow tetrazolium salt to an orange formazan dye. This conversion is possible due to the mitochondrial dehydrogenase enzyme which is present in viable cells, therefore, non-viable cells are unable to form the formazan dye.

The ethanol extract of *B. saligna* showed notable antiproliferative activity against the melanoma cells with an $IC_{50}$ value of 31.80±0.35 µg/ml. It was further tested on non-cancerous human keratinocyte cells ($IC_{50}$: 58.65±5.42), and a selectivity index (SI) of 1.84 was calculated, therefore the extract was less cytotoxic towards the human keratinocytes (SI>1). An SI value above one indicates that a sample is more toxic towards the cancer cells than the non-cancerous cells. As a positive control, Actinomycin D, a chemotherapeutic agent which has shown a response in patients with malignant melanoma, was used. Actinomycin D, showed an $IC_{50}$ value of $2.40\times10^3\pm3.36\times10^{-4}$ and $9.20\times10^{-3}\pm6.88\times10^{-5}$ µg/ml against UCT-MEL-1 and HaCat cells respectively and an SI of 3.83 was calculated (FIG. 1).

During bio-assay guided fractionation of the ethanol extract, four major fractions (M1-M4) were obtained. Antiproliferative activity of M1, M2, M3 and M4 on UCT-MEL-1 cells revealed $IC_{50}$ values of 200.03±2.3, 34.78±11.31, 27.30±0.33 and 13.08±0.02 µg/ml respectively of which M4 showed significant antiproliferative activity (P<0.05). Upon further isolation of compounds from M4, one bioactive compound mixture (DT-BS-01) with significant (P<0.001) antiproliferative activity was obtained, which showed a promising SI value of 4.80 with an $IC_{50}$ value of 5.41±0.99 and 26.06±2.47 µg/ml on UCT-MEL-1 and HaCat cells respectively (FIG. 1). This was later identified as a mixture of two isomers, ursolic acid (UA) and oleanolic acid (OA).

Cell Morphology-Light Microscopy (Haematoxylin and Eosin Staining)

One of the hallmarks of cancer cells is their ability to evade apoptosis, therefore providing a suitable target for the destruction of cancer cells. The effect of *B. saligna* and DT-BS-01 on the morphology of UCT-MEL-1 and HaCat cells was determined using light microscopy. Light microscopy (haematoxylin and eosin staining) was used to determine the qualitative effect *B. saligna* (30 and 60 µg/ml) and DT-BS-01 (5 and 20 µg/ml) on the morphology of UCT-MEL-1 and HaCat cells. Stock concentrations of the *B. saligna* and DT-BS-01 were prepared at 1 mg/ml. *B. saligna* and DT-BS-01 showed an $IC_{50}$ of approximately 30 and 5 µg/ml on UCT-MEL-1 respectively, whereas on HaCat cells showed an $IC_{50}$ of approximately 60 and 20 µg/ml respectively, therefore these concentrations were selected for this study and all the subsequent studies (excluding the chorioallantoic membrane assay). Exponentially growing UCT-MEL-1 and HaCat cells were seeded at $1.0\times10^5$ cells per well in a 6-well plate and incubated for 24 h at 37° C. at 5% $CO_2$ to allow for cell adherence. Thereafter, cells were exposed to the aforesaid concentrations of *B. saligna* and DT-BS-01, a 0.25 DMSO vehicle control, Actinomycin D at 0.025 µg/ml and cells grown in medium only (untreated) and incubated for a further 48 h. Cells were stained (in the 6-well plate) as described by Berrington & Lall (2012). After staining, sterile PBS was added to all the wells and immediately analysed for morphological changes using a light microscope (Zeiss Primovert).

Figure 2:
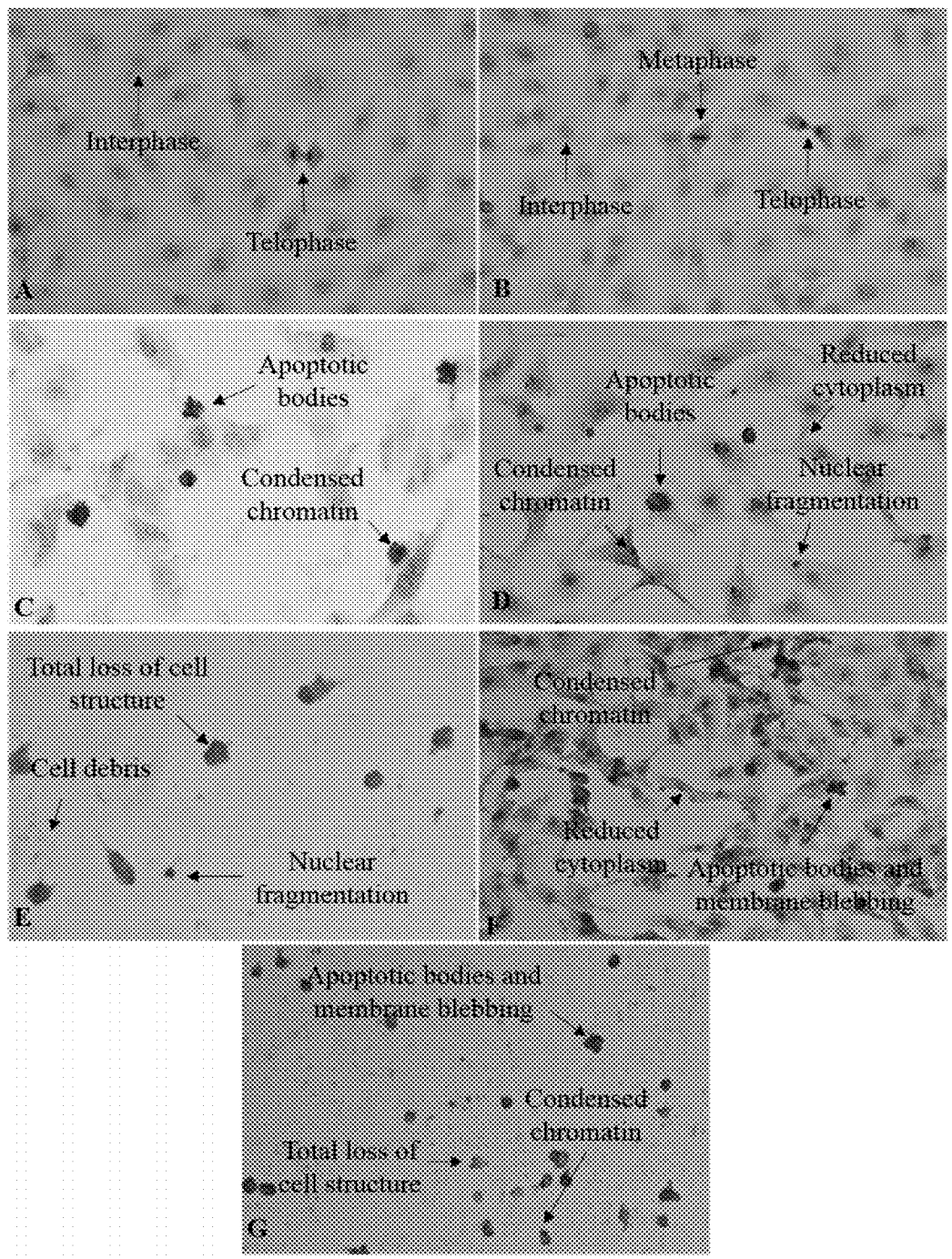
FIG. 2: Panel A—Haematoxylin and eosin staining of human melanoma (UCT-MEL-1) medium-only control (untreated); Panel B—Haematoxylin and eosin staining of UCT-MEL-1 treated with 0.25% DMSO; Panel C—Haematoxylin and eosin staining of UCT-MEL-1 treated with 0.025 µg/ml Actinomycin D; Panel D—Haematoxylin and eosin staining of UCT-MEL-1 treated with 30 µg/ml *B. saligna*; Panel E—Haematoxylin and eosin staining of UCT-MEL-1 treated with 60 µg/ml *B. saligna*; Panel F—Haematoxylin and eosin staining of UCT-MEL-1 treated with 5 µg/ml DT-BS-01; and Panel G—Haematoxylin and eosin staining of UCT-MEL-1 treated with 20 µg/ml DT-BS-01. All images are shown after 48 h of exposure (20 and 40× magnification).
Figure 3:
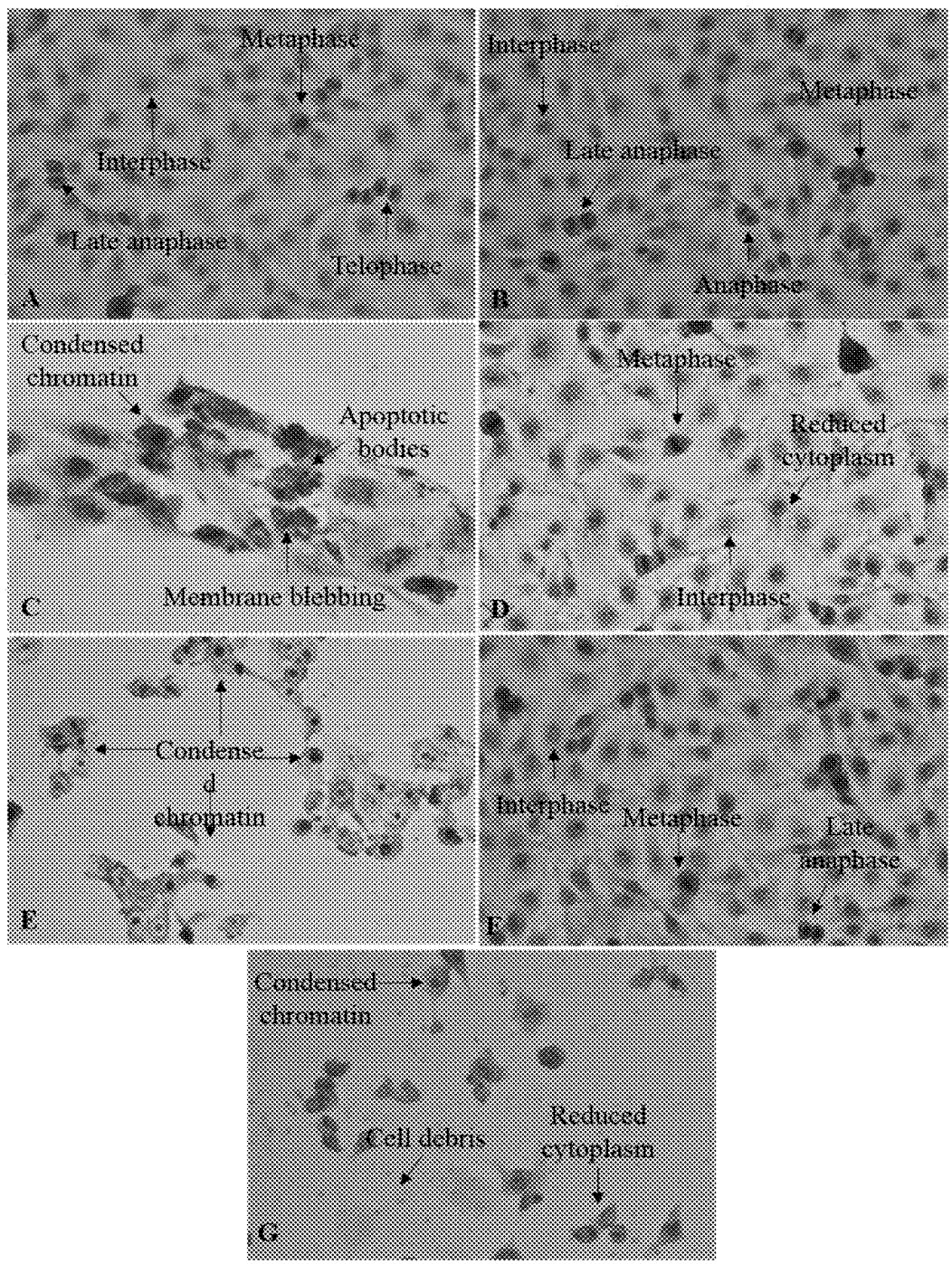
FIG. 3: Panel A—Haematoxylin and eosin staining of human keratinocytes (HaCat) medium-only control; Panel B—Haematoxylin and eosin staining of HaCat treated with 0.25% DMSO; Panel C—Haematoxylin and eosin staining of HaCat treated with 0.025 µg/ml Actinomycin D; Panel D—Haematoxylin and eosin staining of HaCat treated with 30 µg/ml *B. saligna*; Panel E—Haematoxylin and eosin staining of HaCat treated with 60 µg/ml *B. saligna*; Panel F—Haematoxylin and eosin staining of HaCat treated with 5 µg/ml DT-BS-01; and Panel G—Haematoxylin and eosin staining of HaCat treated with 20 µg/ml DT-BS-01. All images are shown after 48 h of exposure (40× magnification).

Light microscopy was performed in order to determine whether cell death, induced by *B. saligna* and the DT-BS-01 was mediated through apoptosis (FIG. 2 and FIG. 3). Apoptosis is described as a programmed cell death in which biochemical and morphological changes occur within the cells. Morphological changes associated with the induction of apoptosis include; condensed chromatin or nucleus, nuclear fragmentation, overall cell reduction, membrane blebbing, loss of membrane integrity, phagocytosis and apoptotic body formation.

The differences in cell densities and cell morphologies between the controls and cells treated with *B. saligna* (30 and 60 µg/ml) as well as DT-BS-01 (5 and 20 µg/ml) were observed. Controls included; cells grown in medium (untreated), cells exposed to 0.25% DMSO and cells treated with 0.025 µg/ml Actinomycin D. In both UCT-MEL-1 and HaCat cells; cells grown in medium (Panel A of FIG. 2 and Panel A of FIG. 3) and cells treated with the vehicle control (DMSO at 0.25%) (Panel B of FIG. 2 and Panel B of FIG. 3) exhibited no lethal effects on the cells and normal stages of cell mitosis were observed. In both cell lines, the positive control, Actinomcyin D displayed characteristic signs of apoptosis such as apoptotic bodies, condensed chromatin and membrane blebbing (Panel C of FIG. 2 and Panel C of FIG. 3). Actinomycin D has been widely reported to induce apoptosis in several human cancer cell lines. *B. saligna* at 30 µg/ml increased the number of apoptotic UCT-MEL-1 cells, which was observed by fragmented nucleus, apoptotic bodies and condensed chromatin; and a dramatic decrease in the number of UCT-MEL-1 cells undergoing mitosis (FIG. 2, Panel D). The HaCat cells, however showed majority of the cells in interphase at 30 µg/ml of *B. saligna* (FIG. 3, Panel D). At an increased concentration of 60 µg/ml *B. saligna*, there was a complete loss of cell structure and low cell densities in the UCT-MEL-1 was observed cells (FIG. 2, Panel E). In the HaCat cells, there was a considerable decrease in mitotic features and cell density as well as an increase in condensed chromatin formation (FIG. 3, Panel E). At 5 µg/ml of DT-BS-01, there was no lethal effect on the HaCat cells (FIG. 3, Panel F), however apoptosis was induced in UCT-MEL-1 cells, at this same concentration, which was characterized by condensed chromatin, apoptotic bodies and membrane blebbing (FIG. 2, Panel F). DT-BS-01 at 20 µg/ml, decreased the density of UCT-MEL-1 cells, induced complete loss of cell structures and signs of apoptosis (FIG. 2, Panel G). In the HaCat cells, 20 µg/ml of DT-BS-01 caused an immense decreased in cell density and no signs of mitosis were observed (FIG. 3, Panel G). These changes in cell morphology suggest that *B. saligna* and DT-BS-01 were able to induce apoptosis in UCT-MEL-1 and HaCat cells. In UCT-MEL-1 cells, apoptosis was induced at lower concentrations than in HaCat cells.

Flow Cytometry-Apoptosis Detection Analysis

Phosphatidylserine (PS) is a lipid, which is present in the inner leaflet of the plasma membrane. The early stages of apoptosis are characterized by an asymmetric membrane due to the translocation of the PS lipid from the inner membrane leaflet to the outer leaflet. Once exposed to the outer cellular environment, Annexin V, which has a high affinity for PS, is able to bind to it. After the early stages of apoptosis have taken place, the plasma membrane integrity starts to disintegrate thereby allowing the uptake of 7-AAD into the cell, which is associated with late apoptosis or necrosis. Therefore, cells which are not undergoing any form of apoptosis or necrosis shows no affinity for either Annexin V or 7-AAD (Annexin V −/7-AAD −); cells undergoing early apoptosis will have an affinity for Annexin V only (Annexin V +/7-AAD−) and cells undergoing late apoptosis or necrosis will be positive for both Annexin V and 7-AAD (Annexin V+/7-AAD+). Using Annexin V and 7-AAD staining can therefore, not distinguish between late apoptosis or necrosis, however can characterize early apoptosis.

The degree of apoptosis was thus measured using the Annexin V-FITC apoptosis detection kit. Exponentially growing UCT-MEL-1 and HaCat cells were seeded in 25 cm$^2$ flasks at a concentration of 1.5×10$^6$ cells/ml in complete medium. The cells were allowed to adhere following 24 h incubation where after the medium was discarded and cells were exposed to 30 and 60 µg/ml of B. saligna as well as 5 and 20 µg/ml of DT-BS-01 respectively. Actinomycin D (0.025 µg/ml) was used as a positive control for apoptosis to occur. Other controls included a medium (untreated) and 0.25% DMSO vehicle control. After 48 h of exposure, cells were trypsinized and 1.0×10$^6$ cells were double-stained with annexin V-FITC and 7-Amino-Actinomycin (7-AAD), according to the manufacturer's protocol (Cat. No. 559763) (BD Pharmingen™, 2008) (BD Biosciences, San Jose, CA, USA). Briefly, cells were washed with PBS and re-suspended in binding buffer at a concentration of 1.0×10$^6$ cells/ml. Cells (1.0×10$^5$) were transferred to separate 5 ml culture tubes for each sample and 5 µl each of annexin V-FITC and 7-ADD was added and incubated for 15 min. An additional 400 µl binding buffer was added to each culture tube and the fluorescence was measured using an Accuri C6 flow cytometer (BD Biosciences, San Jose, CA, USA). Data from at least 10,000 cells were analyzed using the BD Accuri C6 software.

In both cell lines the medium and 0.25% DMSO control, showed a high percentage of viable cells (>94%), indicating that DMSO did not affect cell growth. Both B. saligna and DT-BS-01 increased cell death in a dose-dependent manner in both the UCT-MEL-1 and HaCat cells. The extract treated UCT-MEL-1 cells, exhibited a high number of cells in late apoptosis at both 30 (98.3%) and 60 µg/ml (99.3%). Similarly, the extract treated HaCat cells showed majority of the cells in the late apoptosis stages at 30 (90.3%) and 60 µg/ml (98.1%), however more cells, compared to UCT-MEL-1 cells treated with the extract, were viable or in the early apoptosis stage. These results are comparable to those of the positive control Actinomycin D, where 99.2% of UCT-MEL-1 cells were in the late apoptosis stage compared to 90.6% of HaCat cells in the late apoptosis stage. DT-BS-01 on UCT-MEL-1 cells, showed similar results to the extract in that majority of the cells were in late apoptosis stage at 5 (97.5%) and 20 µg/ml (99.9%). On HaCat cells most of the cells were also present in the late apoptosis stage at 5 (84.3%) and 20 µg/ml (97%), however the amount of late apoptotic cells was higher in the UCT-MEL-1 cells (FIG. 4). It is evident that UCT-MEL-1 cells are more susceptible to cell death when exposed to the different concentrations of the B. saligna extract, DT-BS-01 and positive control as compared to the non-cancerous HaCat cells, which is in agreement with the antiproliferative results. Both B. saligna and DT-BS-01 induced apoptosis in UCT-MEL-1 and HaCat cells in a dose-dependent manner, however at a very low percentage as most of the cells were found in the late apoptotic stage. It is hypothesized that if the cells were treated at the same concentration of the samples but for a shorter time interval, more cells could have been present in the early apoptotic stage. Apoptosis was also qualitatively observed in the light microscopy studies when cells were stained with haematoxylin and eosin, thereby confirming the induction of apoptosis by B. saligna and DT-BS-01.

Example 3

Nitric Oxide Scavenging Activity and Cyclooxygenase-2 Inhibition

Nitric Oxide Scavenging Activity

B. saligna and DT-BS-01 were tested for NO radical scavenging activity by using the Greiss-Ilosvoy's reaction according to the method by Mayur et al (2010) with slight modifications. Stock concentrations of the B. saligna extract, DT-BS-01 and the positive control ascorbic acid, were prepared at 10 mg/ml in ethanol. Briefly, 90 µl of distilled water was added to the top row of a 96-well microtitre plate and 50 µl to the rest of the wells in the plate. Ten microliters of the extract, DT-BS-01 and ascorbic acid were added to the top well of a 96-well plate, in triplicate. Serial dilutions of the samples were prepared at final concentrations ranging from 15.63-2000 µg/ml. Ethanol was used as the negative control. To each well 50 µl sodium nitroprusside (10 mM) was added and the plates were incubated at room temperature for 90 min. Thereafter, 100 µl Griess reagent was added to all the wells, except for the blank plates where distilled water was added. The absorbance was read after 5 min at 546 nm using a BIO-TEK power-wave XS plate reader. All samples were tested in triplicate. The percentage inhibition of the samples was calculated using the below equation.

$$\% \text{ scavenging(inhibition)activity} = \frac{\text{Abs control} - \text{Abs sample}}{\text{Abs control}} \times 100$$

Where $\text{Abs}_{control}$ is the absorbance of NO radical+ethanol control; $\text{Ab}_{sample}$ is the absorbance of (NO radical+sample OR positive control)−(blank values of corresponding sample). The $IC_{50}$ values for each sample were calculated using GraphPad Prism 4 software.

B. saligna and DT-BS-01 showed dose-dependent scavenging activity of NO with an $IC_{50}$ value of 297.2±5.43 and 103.9±6.88 µg/ml respectively. The activity of these two samples was compared to the positive control, ascorbic acid, which showed an $IC_{50}$ value of 62.46±0.46 µg/ml (Table 1). At a concentration of 500 µg/ml, B. saligna, DT-BS-01 and ascorbic acid showed 54.44±0.1, 76.57±4.11 and 75.70±0.15% NO radical scavenging activity respectively. The percentage scavenging activity of DT-BS-01 was statistically similar to that of ascorbic acid at 500 µg/ml. Both B. saligna and DT-BS-01 showed moderate inhibition of NO and therefore, should be considered for their inhibitory activity of intracellular NO.

TABLE 1

Inhibitory effect of B. saligna and DT-BS-01
against the NO free radical and the COX-2 enzyme.

| Samples | NO$^a$ IC$_{50}$$^b$ ± SD in μg/ml | COX-2$^c$ IC$_{50}$ ± SD in μg/ml |
|---|---|---|
| B. saligna | 297.20 ± 5.43 | 28.84 ± 1.18 |
| DT-BS-01 | 103.90 ± 6.88 | 18.83 ± 1.19 |
| Positive control $^d$ | 62.46 ± 0.46 | 1.09 ± 0.01 |

$^a$Nitric oxide;
$^b$Fifty percent inhibitory concentration;
$^c$Cyclooxygenase-2;
$^d$ Positive controls for NO scavenging assay (ascorbic acid) and COX-2 inhibition assay (ibuprofen)

Cyclooxygenase-2 Inhibition

The potential of *B. saligna* and DT-BS-01 to inhibit human recombinant cyclooxygenase-2 (COX-2) enzyme was determined by measuring the concentration of PGE$_2$ after treatment with the various samples and compared to the DMSO vehicle control. The assay was performed as described by Reininger and Bauer (2006). To each well of a 96-well plate, 5 μl of the COX-2 enzyme (0.5 units/well) was added to 180 μl of 100 mM TRIS buffer (pH 8.0) containing 5 μM porcine hematin, 18 mM L-epinephrine, and 50 μM Na$_2$EDTA as co-factors. Stock concentrations of *B. saligna* and DT-BS-01 were prepared at 10 mg/ml in DMSO. Thereafter, 10 μl of *B. saligna* and DT-BS-01 was added to the wells with final concentrations ranging from 2.5-160 μg/ml. Controls included a 5% DMSO vehicle control and a positive control Ibuprofen (10 μM, 2 μM, 0.4 μM). After 5 min, the reaction was initiated by adding 5 μl of 10 μM arachidonic acid. The plate was incubated at room temperature for a further 20 min. Finally 10 μl of 10% formic acid was added to stop the reaction. Quantification of PGE$_2$, which is the main product of the reaction, was achieved by PGE$_2$ ELISA kit after the dilution of samples into a ratio 1:15 according to the manufacturers protocol (Cat. No. ADI-900-001) (Enzo Life Sciences, Inc, Farmingdale, New York, USA) (Enzo Life Science, 2016). The absorbance, corresponding to the concentration of PGE$_2$, was measured at 405 nm using a BIO-TEK powerwave XS plate reader. The results were expressed as percentage inhibition of PGE$_2$ synthesis in comparison with the blank using the below equation.

$$\% \text{ inhibition of } PGE2 = \frac{100 - [PGE2]\text{sample}}{[PGE2]\text{control}} \times 100$$

Where [PGE$_2$]$_{sample}$ is the concentration of PGE$_2$ (pg/ml) produced when treated with the sample OR positive control and [PGE$_2$]$_{control}$ is the concentration of PGE$_2$ (pg/ml) produced when treated with the 5% DMSO vehicle control. The IC$_{50}$ value of *B. saligna* and DT-BS-01 were calculated using Microsoft Excel 2013.

Figure 5:
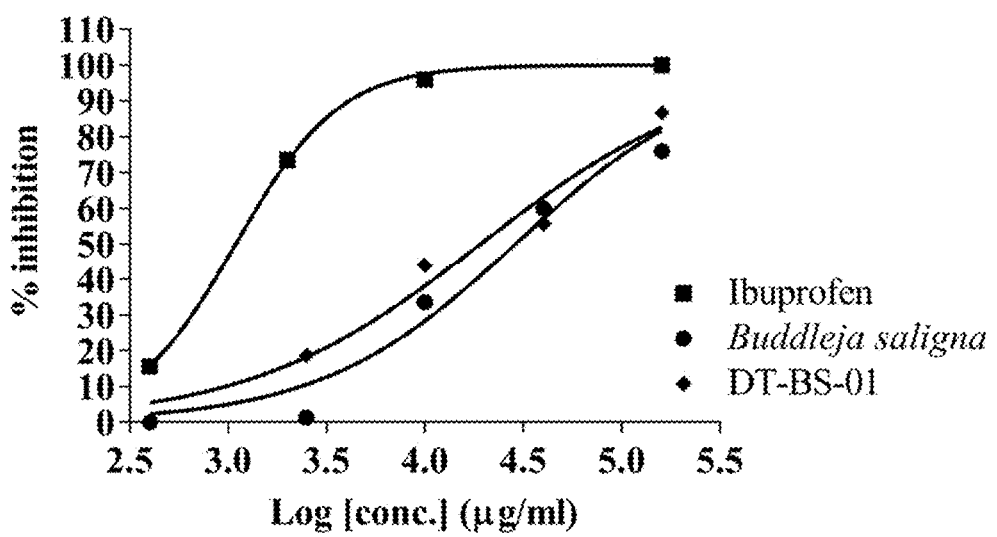
FIG. 5: Dose-dependent curves of *B. saligna* (2.5-160 µg/ml) and DT-BS-01 (2.5-160 µg/ml) on COX-2 mediated $PGE_2$ production. Controls included Ibuprofen (0.4-10 µg/ml) as the positive control and 10% DMSO as the negative control. Data shown are mean±SD (n=3). Statistical analysis was done using one-way analysis of variance (ANOVA) followed by Tukey's multiple comparison test using the GraphPad Prism statistical software where *$P<0.05$, $P<0.01$ and *$P<0.001$ was statistically significant.

In the cell free enzyme inhibition assay, both samples were able to inhibit the production of PGE$_2$ in a dose-dependent manner with an IC$_{50}$ value of 28.84±1.18 and 18.83±1.19 μg/ml for *B. saligna* and DT-BS-01 respectively (Table 1; FIG. 5). DT-BS-01 has statistically higher inhibitory activity (P<0.001) than *B. saligna*. The activity was compared to that of the positive control, Ibuprofen, which showed an IC$_{50}$ value of 1.09±0.01 μg/ml. At a concentration of 10 μg/ml, *B. saligna*, DT-BS-01 and Ibuprofen showed 33.60±4.46, 44.00±7.99 and 95.88±1.54% inhibition of COX-2 respectively. At an increased concentration of 160 μg/ml, the percentage inhibition of *B. saligna* and DT-BS-01 increased to 75.95±2.79 and 86.64±3.57% respectively.

Due to the ability of both the plant extract and DT-BS-01 to directly inhibit the COX-2 enzyme, a further consideration should be to determine whether the samples are able to inhibit the mRNA and protein expression of COX-2 in UCT-MEL-1 cells. In a study by Xu et al (2007), a boiled aqueous extract of *Lonicera japonica* was able to directly inhibit the COX-2 enzyme with an IC$_{50}$ of 15 mg/mL, whereas at an IC$_{50}$ of 5 mg/ml the extract was able to significantly inhibit the protein expression of COX-2 in IL-1β induced COX-2 in A549 lung cancer cells. However, at 5.4 mg/ml, the extract did not significantly inhibit the mRNA expression of COX-2 in A549 cells, suggesting that the extract acts translationally or post-translationally rather than on a transcription level. This suggests that the extract of the present invention could potentially inhibit the protein or mRNA expression of COX-2 in UCT-MEL-1 cells and therefore, should be considered for future studies.

Example 4

Cytokine Analysis

The levels of cytokine production (Interleukin (IL)-8, -1β, -6, -10 & -12μ70; and tumour necrosis factor alpha (TNF-α)) from cell supernatant were measured using the BD™ Cytometric Bead Array (CBA) Human Inflammatory Cytokine kit according to the manufacturer's protocol (Cat. No. 551811) (BD Biosciences, San Jose, CA, USA) (BD, 2008). Briefly, UCT-MEL-1 cells were plated at a concentration of 1.0×10$^5$ cells/well in a 24-well plate with complete medium to allow for cell adherence. After 24 h, the medium was removed and replaced with fresh complete medium. Stock concentrations of *B. saligna* and DT-BS-01 were prepared at 1 mg/ml. The cells were treated with final concentrations of the extract at 30 and 60 μg/ml and DT-BS-01 at 5 and 20 μg/ml. Controls included a 0.25% DMSO vehicle control and cells grown in medium (untreated). All samples included 1 μg/ml phytohaemagglutinin (PHA) for the stimulation of cytokines. After the incubation period, the cells were centrifuged at 980 rpm for 5 min to collect the cell free supernatant and analyse the concentration (in pg/ml) of cytokines using the BD™ Accuri C6 cytometer (BD Biosciences, San Jose, CA, USA). The percentage inhibition was calculated using the following equation:

$$\% \text{ inhibition} = \frac{[\text{cytokine}]\text{medium} - [\text{cytokine}]\text{sample}}{[\text{cytokine}]\text{medium}} \times 100$$

Where [cytokine]medium is the concentration (pg/ml) of the cytokine expressed in cells which contained medium only (untreated) and [cytokine]$_{sample}$ is the concentration (pg/ml) of the cytokine expressed in cells which contained the sample or DMSO.

Figure 6:
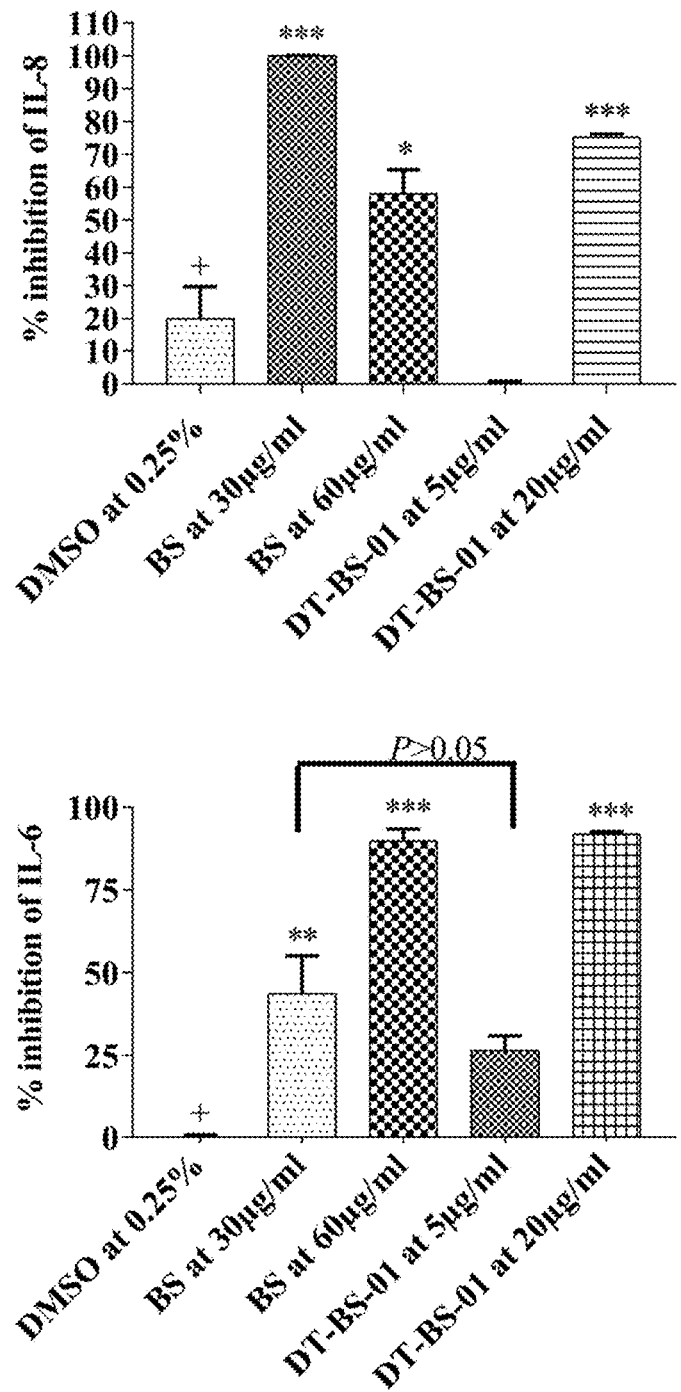
FIG. 6: Effect of *B. saligna* (BS), DT-BS-01 and controls on (a) IL-8 and (b) IL-6 production in human melanoma (UCT-MEL-1) cells. UCT-MEL-1 cells were treated with various concentrations of *B. saligna* (30-60 µg/ml) and DT-BS-01 (5-20 µg/ml) respectively, both with the addition of PHA (1 µg/ml), to determine the production of IL-8 and IL-6 after 24 h. DMSO at 0.25% served as the control. Data shown are mean±SD (n=3). *$P<0.05$, $P<0.01$ and *$P<0.001$ compared with the DMSO (0.25%) control (+). Statistical analysis was done using one-way analysis of variance (ANOVA) followed by Tukey's multiple comparison test using the GraphPad Prism statistical software.

During an incubation period of 24 h, *B. saligna* (30 and 60 μg/ml) and DT-BS-01 (5 and 20 μg/ml), as well as the DMSO (0.25%) control showed 100% cell viability and therefore, no toxicity of UCT-MEL-1 cells was observed. There was no production of IL-1β, IL-10, IL-12p 70; and TNF-α in the PHA stimulated UCT-MEL-1 cells (data not shown), however IL-6 and IL-8 was produced. The difference in the production of IL-8 and IL-6 between the DMSO control and cells grown in medium only (untreated), was not significant (P>0.05) signifying that DMSO did not significantly inhibit or stimulate the production of IL-8 or IL-6 in UCT-MEL-1 cells when compared to the medium control. The calculated percentage inhibition was therefore compared to the DMSO vehicle control (+), which inhibited IL-6 and IL-8 by 0.1±0.98 and 20.08±13.6% respectively. *B. saligna* was able to significantly inhibit the production of IL-6 at both 30 and 60 µg/mi by 43.73±16.16 (P<0.01) and 89.90±4.97% (P<0.001) respectively. This was comparable to the inhibitory activity found against IL-8, where a significant inhibition of 100±0.2 (P<0.001) and 58.02±10.26% (P<0.05) was noted at 30 and 60 µg/mi respectively (FIG. 6). It was interesting to note that *B. saligna* inhibited IL-8 more at a lower concentration of 30 µg/mi than at a higher concentration of 60 µg/mi. Moreover, treatment with DT-BS-01 at 5 µg/mi showed no significant inhibition (P>0.05) of IL-8 or IL-6 when compared to DMSO (+), with an inhibition of 0.10±0.99 and 26.55±6.30% respectively. However when compared to *B. saligna* at 30 µg/mi, there was no significant difference (P>0.05) in the % inhibition of IL-6, suggesting that DT-BS-01 was able to inhibit IL-6. At an increased concentration of 20 µg/mi DT-BS-01, both the concentration of IL-8 and IL-6 were significantly (P<0.001) reduced by 75.30±1.27 and 91.86±1.09% respectively (FIG. 6).

Example 5

Sphingosine-Kinase 1 Inhibition

The levels at which the UCT-MEL-1 cells secrete the sphingosine-kinase 1 protein, were evaluated using flow cytometry by detecting FITC-labelled sphK-1 antibody. A method similar to that by Lafarge et al (2007) was used to perform the experiment with modifications. UCT-MEL-1 cells were plated at a concentration of $5.0 \times 10^5$ cells/ml in T25 flasks and incubated at 37° C. and 5% $CO_2$ for 24 h to allow for cell adherence. After 24 h, the medium was removed and the cells treated with the samples. *B. saligna* was tested at final concentration of 30 and 60 µg/ml whereas DT-BS-01 was tested at 5 and 20 µg/ml. Controls included a 0.25% DMSO vehicle control, cells grown in medium (untreated) and cells exposed to the positive control, 3 µM N, N-dimethyl sphingosine (DMS). The cells were incubated for a further 20 min, where after the medium and removed and the cells washed with phosphate buffer saline (PBS) and detached using 1 mL trypsin-EDTA (0.25% trypsin containing 0.01% EDTA). After cell detachment, the trypsin was inactivated by adding complete medium and the contents of the flasks transferred into separate 15 mL falcon tubes and centrifuged at 980 rpm for 10 min. Thereafter, the pellets were washed twice with PBS and re-centrifuged. The pellets were re-suspended in fixation buffer (BD Cytofix™ Cat. No. 554655; BD Biosciences, 2015a) and incubated for 30 min. Thereafter, the cells were centrifuged at 980 rpm for 10 min and washed twice using PBS. After centrifugation, the cells were re-suspended in permeation buffer (BD Phosflow™ Cat. No. 558050; BD Biosciences, 2015b) to a concentration of $2 \times 10^5$ cells/ml. The UCT-MEL-1 cells were then stained with FITC-labelled SphK1 antibody (Abcam Cat. No. ab95400) (Abcam, 2017). Data from at least 10,000 cells were analysed using the BD™ Accuri C6 cytometer (Johannesburg, South Africa).

Figure 7:
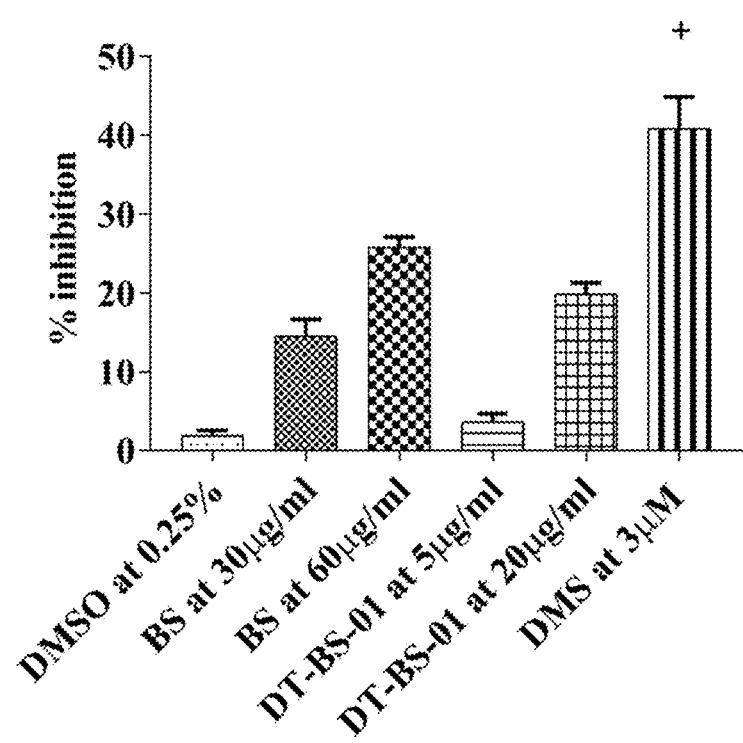
FIG. 7: Percentage inhibition of sphingosine kinase 1 (sphK1) detected in vitro in human melanoma (UCT-MEL-1) cells. Cells were treated with various concentrations of *B. saligna* (30 and 60 µg/ml) and DT-BS-01 (5 and 20 µg/ml) for 20 min. Controls included the positive control, N,N-dimethylphingosine (DMS) (3 µM), DMSO (0.25%) vehicle control and cells grown in medium. Data was expressed as mean±SD (n=2). *$P<0.05$, $P<0.01$ and *$P<0.001$ compared with DMS (+) using the Tukey's Multiple Comparison Test.

The untreated cells were able to express sphK1 by 62.83±4.5 which was comparable to that of the DMSO control that expressed sphK1 by 61.26±2.50% (data not shown). There was a negligible difference between the levels of sphK1 expression in the DMSO and the medium control, which showed that DMSO did not have a negative effect of the expression of sphK1. The positive control, DMS, was able to significantly (P<0.001) inhibit the amount of sphK1 by 40.81±5.7% when compared to DMSO, however neither *B. saligna* nor DT-BS-01 were able to inhibit the levels of sphK1 when compared to DMS. *B. saligna* showed an inhibition of 14.51±3.1 and 25.82±1.8% at 30 and 60 µg/ml respectively, whereas DT-BS-01 inhibited sphK1 by 3.59±1.5 and 19.91±2.0% at 5 and 20 µg/ml respectively (FIG. 7). Even though the samples were not comparable to the DMS positive control, *B. saligna* at 30 (P<0.05) and 60 µg/ml (P<0.01) as well as DT-BS-01 at 20 µg/ml (P<0.01) were able to significantly inhibit sphK1 when compared to DMSO, indicating that these sample did show moderate inhibitory activity.

In a study by Madhunapantula et al (2012), melanoma cells were found to have 1.8-24 fold higher levels of sphK1 than normal melanocytes and that the highest levels of sphK1 were found in vertical growth phase cells. This study further emphasizes the need for new targets for the treatment of melanoma and that sphK1 might provide this new target. Madhunapantula et al (2012) found that by targeting sphK1 using siRNAs or SKI-I, an inhibitor of sphk1, repressed the growth of melanoma cells and increased the sensitivity of melanoma cells to therapeutic agents by triggering apoptosis through increased caspase-7 activity and cleavage of PARP.

Example 6

Quantification of In Vitro VEGF

Exponentially growing UCT-MEL-1 and HaCat cells were seeded at a concentration of $1.0 \times 10^5$ cells/well in a 24-well plate with complete medium to allow for cell adherence. After 24 h, the medium was removed and replaced with fresh complete medium. Stock concentrations of the *B. saligna* extract and DT-BS-01 were prepared at 1 mg/ml. The cells were treated with final concentrations of the *B. saligna* at 30 and 60 µg/ml; and DT-BS-01 at 5 and 20 µg/ml. Controls included a 0.15% DMSO vehicle control, cells grown in medium only and cells exposed to the positive control, ursolic acid at final concentrations of 6 µg/ml. After 6 h of treatment, the plates were centrifuged at 980 rpm for 10 min and the supernatant collected for quantification of VEGF using an ELISA kit (ThermoFisher Scientific, Johannesburg, South Africa) (Thermo Fisher, 2017). The cells viability was further determined using XTT at a final concentration of 0.3 mg/ml. The quantification of VEGF was performed according to the manufacturer's protocol (Novex® Cat #KHG0111) using a VEGF standard curve.

The levels of VEGF secreted by UCT-MEL-1 and HaCat cells were determined after 6 h incubation with *B. saligna* and DT-BS-01. Untreated UCT-MEL-1 cells did not secrete VEGF, suggesting that the cells did not actively produce VEGF in vitro (data not shown). Due to these findings, HaCat cells were used to quantify the concentration of VEGF after treatment with *B. saligna* and DT-BS-01 as well as the relevant controls, which included; cells grown in medium only (untreated), cells treated with 0.15% DMSO vehicle control and the positive control, ursolic acid at 6 µg/ml. The HaCat cell viability was determined after treatment with the various samples and controls in order to determine whether inhibition of VEGF could have been due to a decrease in cell viability. Cell viability was determined as 97.45±7.25 for DMSO, 80.16±6.30 for *B saligna* at 30 µg/ml, 2.39±0.75 for *B saligna* at 60 µg/ml, 94.68±5.62 for DT-BS-01 at 5 µg/ml, 69.71±3.76 for DT-BS-01 at 20 µg/ml, and 96±3.62% for ursolic acid.

Untreated HaCat cells were able to express VEGF at a concentration of 127.50±1.25 µg/ml after 6 h of incubation.

Figure 8:
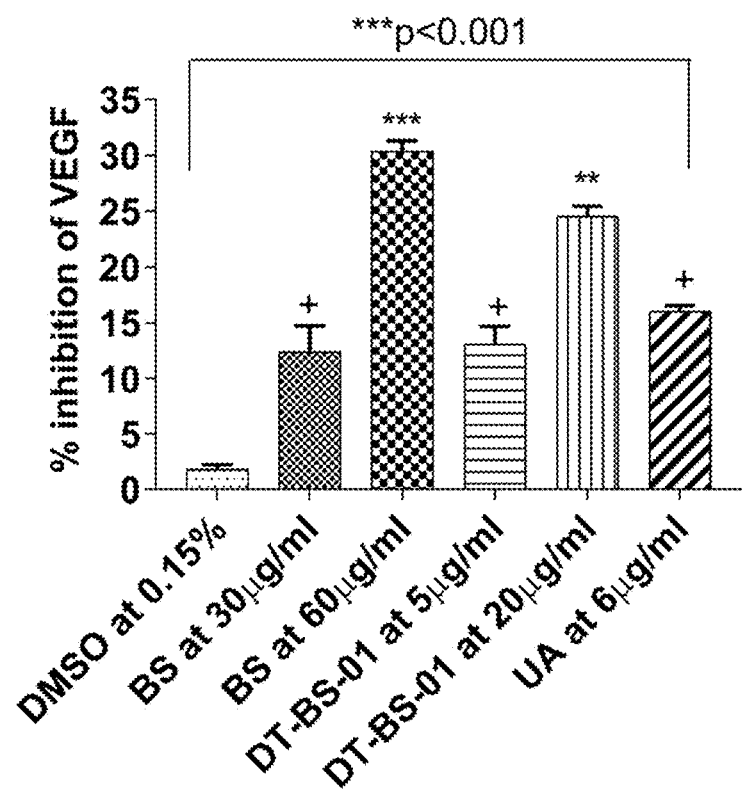
FIG. 8: Percentage inhibition of vascular endothelial growth factor (VEGF) detected in vitro in human keratinocytes (HaCat) using a human VEGF ELISA kit. Cells were treated with various concentrations of *B. saligna* (30 and 60 µg/ml) and DT-BS-01 (5 and 20 µg/ml) for 6 h. Controls included the positive control, ursolic acid (6 µg/ml), DMSO (0.15%) vehicle control and cells grown in medium. Data was expressed as mean±SD (n=3). $P<0.01$ and *$P<0.001$ compared with ursolic acid (+) using the Tukey's Multiple Comparison Test. Samples statistically similar to ursolic acid were identified (+).

DMSO at 0.15% showed similar results and expressed 125.98±1.67 µg/ml of VEGF, and therefore was statistically similar to that of the medium control (P>0.05), signifying that DMSO did not alter the concentration of VEGF (FIG. 8). Compared to the DMSO control, ursolic acid was able to significantly inhibit (P<0.001) the production of VEGF by 16.01±0.93%. *B. saligna* at 30 µg/ml and 5 µg/ml DT-BS-01 were able to significantly inhibit the production of VEGF by 12.42±4.03 and 13.07±2.81% respectively and showed statistically similar activity to that of ursolic acid (+). At an increased concentration of both 60 µg/ml *B. saligna* and 20 µg/ml DT-BS-01, the inhibition of VEGF increased significantly to 30.39±1.60 (P<0.001) and 24.51±1.60% (P<0.01) respectively (FIG. 8). However, due to the decrease in the cell viability when treated with 60 µg/ml *B. saligna* and 20 µg/ml of DT-BS-01, the inhibition of VEGF could potentially be due to cell death. In conclusion, these finding indicate that *B. saligna* and DT-BS-01 are able to significantly inhibit the production of VEGF at the active antiproliferative concentration of 30 µg/ml of *B. saligna* and 5 µg/ml DT-BS-01.

In a melanoma (SK-MEL-2) CAM model, OA was able to reduce the angiogenic potential of the melanoma, whereas UA did not inhibit the density of the capillaries within the CAM. In this same study the cytotoxic effect of UA was greater than OA against SK-MEL-2. The authors therefore suggested testing UA and OA in combination to determine whether there is any synergistic or additive effect (Caunii et al., 2017). The inventors of the present invention identified DT-BS-01 as a mixture of OA and UA and found the mixture to have significant antiproliferative effect against UCT-MEL-1 melanoma cells as well as inhibiting VEGF, therefore testing DT-BS-01 for its in vivo ability to inhibit angiogenesis in the CAM assay is of great relevance and could possibly show significant results.

Example 7

Photoprotective Activity

The in vivo sun protection factor (SPF) assessment of *B. saligna*, at a concentration of 6.0 mg/ml (10% (v/v)) in a sunscreen formulation, was performed according to the South African Bureau of Standard (SANS 1557) and the European Colipa ISO 24444 International Standard. All volunteers signed informed consent before the study commenced. During the study 10 healthy human volunteers were recruited all with skin phototypes II. Briefly, a xenon lamp was used to induce UV at three different sites on the skin; unprotected skin (MEDu), skin protected with and SPF 15 reference standard (MEDp) and skin protected with the sunscreen formulation containing *B. saligna* extract (MEDp), where MED represents the lowest dose of UV needed to induce erythema after 16-24 hrs. The concentration of samples used on the skin was 2 mg/cm². The results were calculated by the original values (n=10) and expressed as mean. The SPF was calculated using the following equation:

$$SPF = \frac{MEDp}{MEDu}$$

The SPF of the sunscreen containing the *B. saligna* plant extract was compared to that of the standard.

The in vitro ultraviolet A (UVA) assessment of *B. saligna*, at a concentration of 6.0 mg/ml (10% (v/v)) in a sunscreen formulation, was performed according to the European Colipa ISO 24443 international standard. Briefly, the sunscreen sample (1.3 mg/cm²) was applied to a polymethylmethacrylate (PMMA) plate and spread evenly over the roughened surface. The plate was stored in the dark at room temperature for 30 min before use. A blank plate, which was treated with enough glycerine to coat the entire surface, was included. Thereafter, the plates were placed in the light-path of a UV-2000S) ultraviolet transmittance analyser (Labsphere, USA). The absorbance of UV radiation through the samples was measured from 290-400 nm at 1 nm intervals on 4 different locations. Thereafter, the plates were UV-irradiated and new absorbance measurements were conducted. A total of four test plates were prepared to establish the UVA protection activity of the sample by calculating the final UVA protection factor (UVAPF), the SPF in vivo UVAPF ratio and the critical wavelength.

*B. saligna*, at a final concentration of 10% (v/v) in a sunscreen formulation, showed an SPF of 16.1±0.7 in an SPF in vivo clinical trial. Furthermore, when tested in an in vitro clinical trial for its protective effects against UVA, the sunscreen formulation, which contained *B. saligna*, showed an UVAPF of 6.45±0.06, an SPF in vivo UVAPF ratio of 2.33, an UVA balance of 39% and a critical wavelength of 379.50 nm. Under the current SANS 1557 standard, a sample with a critical wavelength of 370 nm or more, may make the claim of "broad spectrum". Furthermore, samples with a UVA balance of 33% and a critical wavelength of 370 nm or more may make the claim of "UVA protection". Therefore, the sunscreen formulation may claim an SPF of 15 with broad spectrum application which has UVA protection properties.

Example 8

Ex Ovo Chorioallantoic Membrane Assay

An ex ovo chorioallantoic membrane assay (CAM) was performed according to the method as described by Roma-Rodrigues et al (2016), in order to determine the effect that an ethanolic extract of *Buddleja saligna* and the isolated compound mixture DT-BS-01 had on angiogenesis. The assay was performed according to the Directive 2010/63/EU of the European Parliament and the council of 22 Sep. 2010 on the protection of animals used for scientific purposes.

Fertilized eggs were incubated for 72 h at 37° C. and 90% (v/v) relative humidity. During the incubation, eggs were gently turned twice a day to prevent adherence of the yolk sack to the shell. Thereafter, the eggs were opened into weighing boats (L89×W89×H25 mm) with the yolk sacks and blood vessels facing upwards. Weighing boats, with the same dimensions and with holes punctured in the sides, were used to cover the opened eggs. Once the opened eggs had stabilized for an additional 24 h at 37° C. and 90% (v/v) relative humidity, four sterilized silicone O-rings, with an internal diameter of 8 mm, were placed on the blood vessels as depicted by Roma-Rodrigues et al (2019). To each O-ring, 40 µl of sample was added, of which each egg contained at least one control. The controls included phosphate buffered saline (PBS) and a vehicle treated control (3% DMSO). The *Buddleja saligna* ethanolic extract was tested at a concentration of 15 µg per egg and the compound mixture (DT-BS-01) was tested at 2.5 µg per egg. After the addition of the samples to the O-rings, the eggs were incubated for a further 24 h at 37° C. and 90% (v/v) relative humidity.

Images of each of the O-rings were taken at 0 h and 24 h of incubation with the test samples and controls using a digital USB microscope camera (Opti-Tekscope OT-V1). Images were analysed using the Fiji ImageJ Software with the Analyze Skeleton plugin as described by Roma-Rodrigues et al (2016). The ability of a sample to reduce the percentage of blood vessels was calculated relative to the number of blood vessels in the vehicle treated control.

Figure 9:
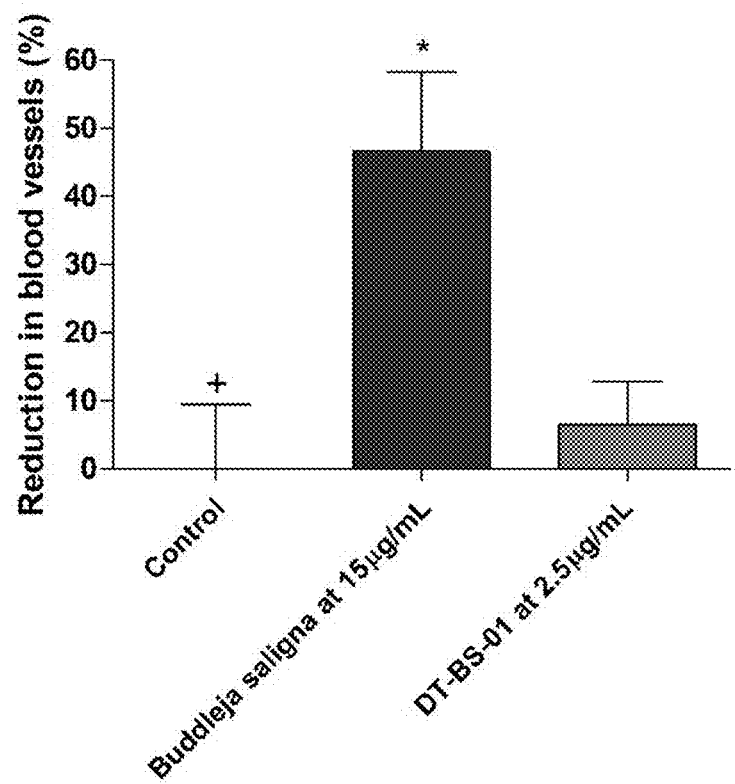
FIG. 9: Reduction of percentage blood vessels (%) when treated with *Buddleja saligna* ethanolic extract (15 µg per egg) and with the compound mixture, DT-BS-01 (2.5 µg per egg), when compared to the vehicle treated control (3% DMSO). Data is represented as mean±SD (n=3), where * represents statistical significance ($P<0.05$) compared to the vehicle treated control (+) using Dunett's multiple comparison test.

From the results depicted in FIG. 9, the ethanolic extract of *Buddleja saligna*, at a concentration of 15 µg per egg, was able to significantly reduce the formation of blood vessels when compared to the vehicle treated control (3% DMSO). A 46.64±16.45% and 6.50±10.86% reduction in blood vessels was noted when the CAM was treated with *B. saligna* and DT-BS-01, respectively. The blood vessel formation in the CAM, when treated with the vehicle control (3% DMSO), was not statistically different (P>0.05) when compared to the PBS control, indicating that DMSO did not reduce the formation of blood vessels at a concentration of 3%.

REFERENCES

Berrington, D. and Lall, N., 2012. Anticancer activity of certain herbs and spices on the cervical epithelial carcinoma (HeLa) cell line. *Evidence-Based Complementary and Alternative Medicine*, 2012.

Caunii, A., Oprean, C., Cristea, M., Ivan, A., Danciu, C., Tatu, C., Paunescu, V., Marti, D., Tzanakakis, G., Spandidos, D. A. and Tsatsakis, A., 2017. Effects of ursolic and oleanolic on SK-MEL-2 melanoma cells: In vitro and in vivo assays. *International journal of oncology*, 51(6), pp. 1651-1660.

Chukwujekwu, J. C., Amoo, S. O. and Van Staden, J., 2013. Antimicrobial, antioxidant, mutagenic and antimutagenic activities of *Distephanus angulifolius* and *Ormocarpum trichocarpum*. *Journal of ethnopharmacology*, 148(3), pp. 975-979.

Lafarge, S., Hamzeh-Cognasse, H., Chavarin, P., Genin, C., Garraud, O. and Cognasse, F., 2007. A flow cytometry technique to study intracellular signals NF-κB and STAT3 in peripheral blood mononuclear cells. *BMC molecular biology*, 8(1), p. 64.

Madhunapantula, S. V., Hengst, J., Gowda, R., Fox, T. E., Yun, J. K. and Robertson, G. P., 2012. Targeting sphingosine kinase-1 to inhibit melanoma. *Pigment cell & melanoma research*, 25(2), pp. 259-274.

Mayur, B., Sancheti, S., Shruti, S. and Sung-Yum, S., 2010. Antioxidant and glucosidase inhibitory properties of *Carpesium abrotanoides* L. *Journal of Medicinal Plants Research*, 4(15), pp. 1547-1553.

Reininger, E. A. and Bauer, R., 2006. Prostaglandin-H-synthase (PGHS)-1 and 2 microtiter assays for the testing of herbal drugs and in vitro inhibition of PGHS-isoenzyms by polyunsaturated fatty acids from *Platycodi radix*. *Phytomedicine*, 13(3), pp. 164-169.

Roma-Rodrigues, C., Heuer-Jungemann, A., Fernandes, A. R., Kanaras, A. G., and Baptista, P. V. 2016. Peptide-coated gold nanoparticles for modulation an angiogenesis in vivo. *International Journal of Nanomedicine* 11, 2633-2639.

Roma-Rodrigues, C., Fernandes, A. R., and Baptista, P. V. 2019. Counteracting the effect of leukemia exosomes by antiangiogenic gold nanoparticles. *International Journal of Nanomedicine* 14, 6843-6854.

Steenkamp, V. and Gouws, M. C., 2006. Cytotoxicity of six South African medicinal plant extracts used in the treatment of cancer. *South African Journal of Botany*, 72(4), pp. 630-633.

Xu, Y., Oliverson, B. G. and Simmons, D. L., 2007. Trifunctional inhibition of COX-2 by extracts of *Lonicera japonica*: direct inhibition, transcriptional and post-transcriptional down regulation. *Journal of ethnopharmacology*, 111(3), pp. 667-670.

The invention claimed is:

1. A method of treating skin cancer in a subject in need thereof, the method comprising administering an effective amount to the subject a crude ethanolic extract from *Buddleja saligna*; wherein the ethanolic extract inhibits angiogenesis but does not inhibit IL-6 or VEGF.

2. A method of reducing skin damage from ultraviolet (UV) radiation in a subject, the method comprising administering an effective amount to the subject a crude ethanolic extract from *Buddleja saligna*; wherein the ethanolic extract inhibits angiogenesis but does not inhibit IL-6 or VEGF.

3. The method of claim 1, wherein the skin cancer is malignant melanoma.

4. The method of claim 1 or 3, wherein the extract inhibits angiogenesis and/or proliferation of cells associated with the skin cancer.

5. The method of claim 1 or 2, wherein the subject is a human.

6. The method of claim 1 or 2, wherein the extract is administered together with a pharmaceutically acceptable carrier.

7. The method of claim 1 or 2, wherein the extract is administered to the subject by topical, parenteral, or oral administration.

* * * * *